United States Patent
Matsuo et al.

(10) Patent No.: US 7,340,942 B2
(45) Date of Patent: Mar. 11, 2008

(54) SENSOR INCLUDING A SENSOR ELEMENT HAVING ELECTRODE TERMINALS SPACED APART FROM A CONNECTING END THEREOF

(75) Inventors: Kouji Matsuo, Aichi (JP); Yuichi Yamada, Aichi (JP)

(73) Assignee: NGK Spark Plug Co., Ltd., Aichi (JP)

( * ) Notice: Subject to any disclaimer, the term of this patent is extended or adjusted under 35 U.S.C. 154(b) by 0 days.

(21) Appl. No.: 11/384,257

(22) Filed: Mar. 21, 2006

(65) Prior Publication Data

US 2006/0220159 A1   Oct. 5, 2006

(30) Foreign Application Priority Data

Mar. 22, 2005   (JP) .............................. 2005-082639

(51) Int. Cl.
  *G01N 7/00*   (2006.01)
(52) U.S. Cl. .................................... 73/31.05
(58) Field of Classification Search .............. 73/23.31, 73/23.32, 31.05, 31.06; 204/424, 426
See application file for complete search history.

(56) References Cited

U.S. PATENT DOCUMENTS

| | | | |
|---|---|---|---|
| 4,556,475 A | 12/1985 | Bayha et al. | |
| 4,636,293 A * | 1/1987 | Bayha et al. | ................ 204/428 |
| 5,573,650 A | 11/1996 | Fukaya et al. | |
| 5,922,938 A * | 7/1999 | Hafele | ........................ 73/23.32 |
| 6,477,887 B1 | 11/2002 | Ozawa et al. | |
| 6,688,157 B2 | 2/2004 | Yamada et al. | |
| 6,866,517 B2 | 3/2005 | Kimata et al. | |
| 2002/0063059 A1 | 5/2002 | Sugiyama et al. | |
| 2003/0074950 A1 | 4/2003 | Yamada et al. | |
| 2005/0126261 A1* | 6/2005 | Matsuda et al. | ........... 73/31.05 |
| 2006/0288759 A1* | 12/2006 | Okumura et al. | .......... 73/31.05 |

FOREIGN PATENT DOCUMENTS

| | | |
|---|---|---|
| JP | 2001-188060 | 7/2001 |
| JP | 2002-296223 | 10/2002 |

* cited by examiner

*Primary Examiner*—Michael Cygan
(74) *Attorney, Agent, or Firm*—Sughrue Mion, PLLC

(57) ABSTRACT

A sensor having a terminal connection structure in which an elongated sensor element (21) is inserted, from its rear end through relative movement, into a metallic-terminal-member retainer. Metallic terminal members (51) are elastically deformed and pressed against corresponding electrode terminals (25) formed on side surfaces (26) of the sensor element. A chamfer (28) is formed on a rear edge of sensor element (21). Rear ends (25*b*) of the electrode terminals (25) are biased from the chamfer (28) toward a front end of the element (21). A flat surface (26*b*) is present between the rear ends (25*b*) of the electrode terminals (25) and a front end (28*a*) of the chamfer (28). During insertion of the element (21), a large force generated when the metallic terminal members (51) pass over the chamfer (28) is not directly applied to the rear ends (25*b*) of the electrode terminals (25), thereby preventing damage to the electrode terminals (25).

5 Claims, 17 Drawing Sheets

SENSOR INCLUDING A SENSOR ELEMENT HAVING ELECTRODE TERMINALS SPACED APART FROM A CONNECTING END THEREOF

BACKGROUND OF THE INVENTION

1. Field of the Invention

The present invention relates to a sensor having a sensor element for detecting a measurement object, such as a gas sensor for detecting the concentration of a certain component in exhaust gas or a like gas; for example, an oxygen sensor, a $NO_x$ sensor, or a HC sensor, or such as a temperature sensor for detecting the temperature of a gas.

2. Description of the Related Art

Conventional sensors employ various kinds of sensor elements (hereinafter, also referred to as elements), such as gas sensor elements, or temperature-sensitive elements, the sensor elements assuming a longitudinally elongated plate-like or rod-like shape. In such a sensor (for example, an oxygen sensor), a sensor element is fixed in the interior of a tubular metallic shell (metallic shell body) having a male-threaded portion to be mounted, for example, to the exhaust gas pipe of an engine. A front-end detection portion thereof projects from the front end of the metallic shell, whereas a rear-end portion thereof projects from the rear end of the metallic shell. In the sensor, usually, a plurality of electrode terminals (terminal electrodes) including electrode terminals used to output a detection output and electrode terminals used to power a heater formed on the element are disposed on opposite side surfaces of a rear end portion of the element while being spaced at electrically insulative intervals in the widthwise direction of the element (laterally). In some cases, in order to establish electrical connection between the electrode terminals and corresponding lead wires extending to the exterior of the sensor, metallic terminal members (metallic terminals or lead frames) connected to corresponding distal ends of the lead wires are pressed against the corresponding electrode terminals by use of their own spring properties so as to abut or be brought into press contact with the electrode terminals (Patent Documents 1 and 2). The metallic terminal members are connected at first ends to corresponding distal ends of the lead wires and are, for example, bent at second ends in a turnback fashion (e.g., in a U-shaped fashion) to thereby form respective plate springs. One leg of each of the U-shaped portions serves as a connection portion (hereinafter, also referred to as an electrode connection portion) which is pressed against the corresponding electrode terminal.

In such a terminal connection structure, as shown in FIG. 12A, metallic terminal members 51 connected to corresponding distal ends of, for example, four lead wires (not shown) are disposed in the interior of a metallic-terminal-member retainer (also called a separator) 71 formed of an electrically insulative material, in a mutually facing fashion while being separated from each other in an electrically insulative condition. As shown in FIG. 12B, a sensor element 21 is inserted, from its rear end 27 through relative movement, between the mutually facing metallic terminal members 51 along its longitudinal direction. By this procedure, the metallic terminal members 51 are elastically deformed outward and are pressed against corresponding electrode terminals 25 formed on side surfaces of the element 21. In other words, insertion of the element 21 forcibly expands outward the space between the facing metallic terminal members 51 against a spring effect of the metallic terminal members 51, and the facing metallic terminal members 51 pinch therebetween the corresponding electrode terminals 25 formed on the side surfaces of the element 21, thereby establishing electrical connection between the electrode terminals 25 and the corresponding metallic terminal members 51. In such a terminal connection structure, for structural reasons, the metallic terminal members 51 are disposed within the metallic-terminal-member retainer 71 such that before connection (before insertion of the element 21), the metallic terminal members 51 are arranged such that a gap (the width of a space) K between the facing metallic terminal members 51 is smaller than the thickness of the sensor element 21 or zero.

In such a terminal connection structure, in order to enhance the reliability of electrical connection, the metallic terminal members 51 must have an intensive spring quality so as to press against the corresponding electrode terminals 25 with a strong spring force in a connected condition. However, intensifying the spring quality of the metallic terminal members 51 increases a force (push-in force) required for inserting the element 21 and involves the risk of undesirable deformation of the metallic terminal members 51 at the time of insertion of the element 21, with resultant deterioration in connection reliability. The reason for this is as follows. The metallic terminal members 51 are formed such that reception portions of the facing metallic terminal members 51 for receiving the element 21 to be inserted fan out toward the element 21 which is to be inserted (fan out downward in the drawing), so as to function as reception guides. Accordingly, at the beginning of insertion of the element 21, edges C of a rear end 27 of the element 21 acutely contact the surfaces of the reception portions of the metallic terminal members 51. For example, in the case where the gap K between the facing metallic terminal members 51 is small, and the metallic terminal members 51 have an intensive spring quality, resistance to insertion (hereinafter, also referred to as insertion resistance) of the element 21 increases, potentially resulting in the metallic terminal members 51 failing to undergo smooth elastic deformation.

For solving the above problem, reducing the insertion resistance of the element is effective. An effective means for reducing insertion resistance is to appropriately chamfer (bevel or round) rear end edges of the element; i.e., edges defined by the rear end surface of the element and the side surfaces of the element on which electrode terminals to be pressed against corresponding metallic terminal members are formed (Patent Document 1). In other words, as shown in FIG. 13, chamfers (chamfered portions) 28 are formed on the rear end 27 of the element 21. Thus, portions of the element 21 which contact the metallic terminal members 51 at the beginning of insertion of the element 21 are not right-angled edges of the rear end 27, but are the chamfers 28, thereby reducing insertion resistance against the metallic terminal members 51 not only at the beginning of insertion but also during the full course of insertion.

Japanese Patent Application Laid-Open (kokai) No. 2001-188060

Japanese Patent application Laid-Open (kokai) No. 2002-296223

3. Problems to be Solved by the Invention

Insertion of the element 21 having the chamfers 28 formed on the rear end 27 prevents undesired deformation of the metallic terminal members 51 by virtue of the aforementioned reduction in insertion resistance of the element 21, or implementation of smooth insertion. However, the following additional problem has been found to arise. In some cases, the electrode terminals 25 of the element 21 to be inserted are damaged; for example, scraped or exfoliated. From tests and analysis of test results, the present inventors found the cause of such damage, as described below.

The electrode terminals are formed on the element as follows: a metallization paste which contains a high-melting-point metal, such as platinum, as a main component is applied by printing to the surface of a green element (ceramic), and then the applied metallization paste and the green element are simultaneously fired. The thickness of the electrode terminals is as thin as tens of μm at most. The rear ends of the electrode terminals 25 of the above-mentioned conventional element 21 are located at the same position as that of front ends 28a of the chamfers 28 (front ends of chamfered portions located on a side toward the front end of the element). In the course of inserting the element 21 having the chamfers 28 formed on the rear end 27, the element 21 slides, through relative movement, on the metallic terminal members 51 from the start of insertion, and a relatively large force which is generated until the metallic terminal members 51 pass over the chamfers 28, is applied directly to the rear ends of the electrode terminals 25 located at the front ends (outermost ends) 28a of the chamfers 28. Since the electrode terminals 25 are thin, and a relatively large force which is generated when the metallic terminal members 51 pass over the chamfers 28 is applied directly to the rear ends of the electrode terminals 25 located at the front ends 28a of the chamfers 28, the metallic terminal members 51 act directly on the corresponding electrode terminals 25 to scrape off the electrode terminals 25 in a frontward direction from their rear ends. The electrode terminals 25 are thus prone to damage. Damage, if any, to the electrode terminals in the terminal connection structure deteriorates the reliability of electrical connection when the sensor (product) is used in actual applications.

SUMMARY OF THE INVENTION

The present invention has been accomplished in view of the above problems associated with a sensor having the afore-mentioned terminal connection structure, and an object of the present invention is to prevent occurrence of damage to the electrode terminals of a sensor element during connection of metallic terminal members to corresponding electrode terminals.

To achieve the above object, in a first aspect (1) the invention provides a sensor comprising: a sensor element including a detection portion formed at a front end portion adapted to face a measurement object, a rear end portion, a plurality of electrode terminals formed on a side surface of the rear end portion, and a chamfer provided on an edge defined by a rear end surface and the side surface having the electrode terminals formed thereon; a plurality of metallic terminal members elastically deformed and pressed against corresponding electrode terminals formed on the side surface of the sensor element so as to engage said sensor element; and an insulating retainer retaining therein said metallic terminal members and surrounding the rear end portion of the sensor element, wherein rear ends of the electrode terminals are spaced apart from a front end of the chamfer, and a flat surface of the sensor element is present between the rear ends of the electrode terminals and the front end of the chamfer.

In a second aspect (2), the invention provides a sensor according to (1) above, wherein the distance between the rear ends of the electrode terminals and the front end of the chamfer as measured on the flat surface along a longitudinal direction of the sensor element is 0.5 mm or more.

In a third aspect (3), the invention provides a sensor according to (1) or (2) above, wherein the distance between the rear ends of the electrode terminals and the front end of the chamfer as measured on the flat surface along the longitudinal direction of the sensor element is longer than the distance along the longitudinal direction between the front end of the chamfer and the rear end surface of the sensor element.

In a fourth aspect (4), the invention provides a sensor according to any one of (1) to (3) above, wherein the metallic terminal members include projections projecting toward corresponding electrode terminals, the projections pressing against the electrode terminals.

In a fifth aspect (5), the invention provides a sensor according to any one of (1) to (4) above, wherein each of the metallic terminal members includes a support portion extending along the longitudinal direction, and a turnback portion extending rearward along the longitudinal direction from a front end of the support portion; the turnback portion including a front end connected to the front end of the support portion and an abutment portion located rearward of the front end and adapted to abut the support portion; and the metallic terminal members are configured such that, in a free state before engaging the sensor element, the abutment portions are separated from the corresponding support portions and such that, as the metallic terminal members engage the front end of the sensor element so as to move the front ends of the turnback portions frontward beyond the front end of the chamfer located on the side toward the front end of the sensor element, the turnback portions are elastically deformed toward corresponding support portions, and the abutment portions come to abut the corresponding support portions.

4. Effect of the Invention:

In insertion of a conventional element whose rear end is chamfered, when metallic terminal members pass, through relative movement, over a chamfer after the element contacts the metallic terminal members, insertion resistance (push-in force) of the element is at a maximum. Since electrode terminals are provided next to the chamfer without any gap between the rear ends of the electrode terminals and the front end of the chamfer, when the metallic terminal members pass over the chamfer, the rear ends of the electrode terminals are subjected to such a strong force on the corresponding electrode terminals (layers) as to scrape or scratch off the electrode terminals in a frontward direction from their rear ends. Notably, herein, the rear end of an electrode terminal is an end of the electrode terminal located on a side toward the rear end of the element, and the front end of a chamfer is an end of the chamfer located on a side toward the front end of the element.

By contrast, even though the sensor element used in the present invention has a chamfer (bevel or round) formed on an edge defined by its rear end surface and the side surface having the electrode terminals formed thereon, the sensor element is formed as follows: the electrode terminals are formed such that rear ends of the electrode terminals are located away from the front end of the chamfer, keeping a gap between them; furthermore, a flat surface is present between the rear ends of the electrode terminals and the front end of the chamfer located on the side toward the front end of the element. Accordingly, during insertion of the element, a large force generated when the metallic terminal members pass over the chamfer is not directly applied to the rear ends of the electrode terminals. Specifically, such a large force by the metallic terminal members is relieved before the metallic terminal members reach the rear end edge of the electrode terminals. After the metallic terminal members slide on the flat surface, insertion resistance has already been greatly reduced. Accordingly, the force applied by the metallic terminal members to the corresponding electrode terminals is reduced to a level low enough to prevent damage to the electrode terminals. In other words, the metallic terminal members merely slide on the corresponding electrode terminals under a low insertion resistance, thereby preventing damage to the electrode terminals.

As described in (2) above, an appropriate length in the longitudinal direction of the above-mentioned flat surface is 0.5 mm or more. Insertion resistance (push-in force) of the element reaches its peak when the metallic terminal members pass over the chamfer towards the front end of the sensor element, and subsequently is greatly reduced. Thus, basically, the presence of the flat surface between the chamfer and the rear ends of the electrode terminals is sufficient, but to secure a sufficient effect of relieving insertion stress on the electrode terminals, the longitudinal length of the flat surface is preferably 0.5 mm or more, more preferably 1 mm or more. On the other hand, in further view of demand for reduction in size (length) of the element, a preferable upper limit of the longitudinal length of the flat surface can be set to 5 mm.

Preferably, as described in (3) above, the longitudinal length between the front and rear ends of the above-mentioned flat surface is longer than a longitudinal distance between the front end of the chamfer and the rear end surface of the sensor element. By employing such a length between the front and rear ends of the flat surface, insertion resistance can further be effectively reduced when sliding the metallic terminal members on the flat surface.

Preferably, as described in (4) above, the metallic terminal members further include projections (protrusions) projecting toward the corresponding electrode terminals and pressing against the electrode terminals. In the terminal connection structure in which the element is inserted, the thus-formed projections abut the corresponding electrode terminals locally or in a concentrated manner and thus in a kind of biting condition. Thus, the contact surface pressure is increased, thereby enhancing the stability or reliability of electrical connection. In the case where a conventional element is combined with the metallic terminal members each having projections formed thereon, when the projections pass over a chamfered portion, insertion resistance further increases due to such projections, thereby further increasing the risk of damage to the electrode terminals. By contrast, the present invention is free from such risk and can enhance the reliability of electrical connection owing to the presence of the flat surface provided between the electrode terminals and the chamfer.

Preferably, as described in (5) above, the metallic terminal members are configured such that, in a free state before complete engagement with the sensor element, the abutment portions are separated from the corresponding support portions and are configured such that, as the metallic terminal members are moved toward the front end of the sensor element from the rear end of the sensor element, the turnback portions are elastically deformed toward the corresponding support portions, and the abutment portions come to abut the corresponding support portions.

As described above, each of the metallic terminal members of the present invention is configured such that a force with which the metallic terminal member presses the side surface of the sensor element differs between a case where the abutment portion of the turnback portion abuts the support portion and a case where the abutment portion is separated from the support portion. More specifically, each of the metallic terminal members is configured such that a dual supporting condition (two-point support condition) where the front end of the turnback portion is connected to the front end of the support portion with the connection portion while the abutment portion of the turnback portion abuts the support portion is greater, in terms of the force with which the metallic terminal member presses the side surface of the sensor element, than a single supporting condition (one-point support condition) where the front end of the turnback portion is connected to the support portion while the abutment portion of the turnback portion remains separated from the support portion. Thus, in the first half of engagement of the metallic terminal members and the sensor element, the turnback portions are in a one-point support condition where the turnback portions are supported by the respective support portions only at their front ends, so that the metallic terminal members are pressed against the corresponding electrode terminals of the sensor element with a relatively small force, thereby effectively suppressing damage to the sensor element which could otherwise result from force applied by the metallic terminal members. After the engagement has been completed, the turnback portions are in a two-point support condition where the turnback portions are supported at two points by the respective support portions, so that the force which the turnback portions apply to the sensor element through their own elastic deformation is greater than that in a one-point support condition, thereby establishing good, firm connection between the metallic terminal members and the corresponding electrode terminals of the sensor element.

In the present embodiment, the metallic terminal members are formed beforehand such that, during engagement of the metallic terminal members and the sensor element, after the front ends of the turnback portions are moved frontward beyond the front end of the chamfer, the turnback portions are elastically deformed toward the corresponding support portions, and the abutment portions come to abut the corresponding support portions. Thus, in engagement of the metallic terminal members and the sensor element, the distance over which the turnback portions move while passing over the chamfer to reach the front side of the chamfer while being supported at two points by the respective support portions can be shortened. Thus, according to the present invention, during engagement of the sensor element and the metallic terminal members which can be firmly connected to the sensor element such that the turnback portions are supported at two points by the corresponding support portions, damage to the electrode terminals of the sensor element can be prevented while the aforementioned beneficial effect of forming a chamfer on the sensor element is realized.

BRIEF DESCRIPTION OF THE DRAWINGS

FIG. 2 shows enlarged views of an element with its intermediate portion omitted, wherein

DESCRIPTION OF REFERENCE NUMERALS

Figure 1:
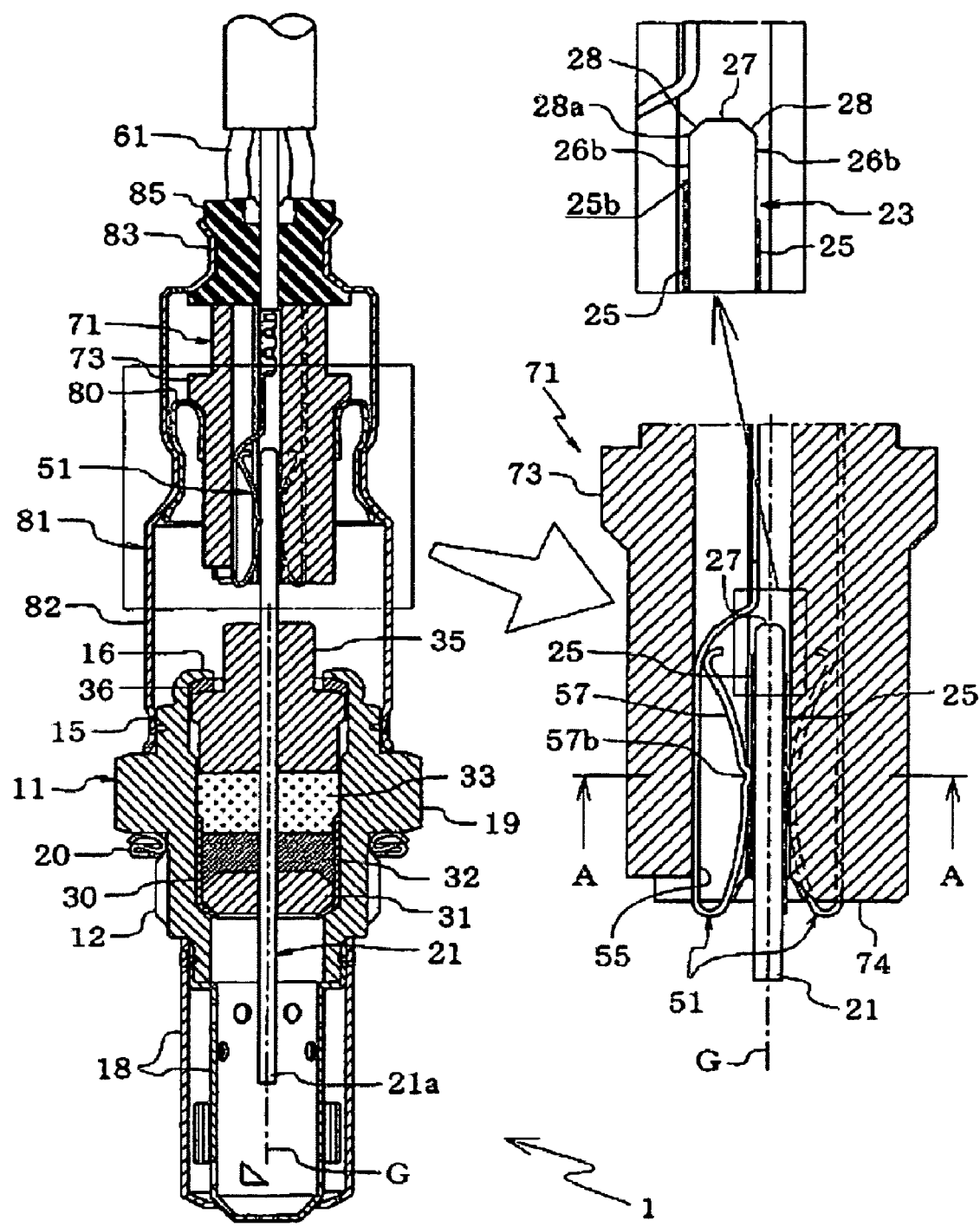
FIG. 1 is a longitudinal sectional view of an embodiment of a sensor according to the present invention, and enlarged views of essential portions of the sensor.

Reference numerals used to identify various structural features in the drawings including the following.
1: sensor
21: sensor element
21a: detection portion
23: rear end portion of element
25: electrode terminal of element
25b: rear end of electrode terminal
26: side surface of element
26b: flat surface of element
27: rear end of element
28: chamfer
28a: front end of chamfer
51: a plurality of metallic terminal members
55: support portion
57: curved portion (turnback portion)
58: end portion (abutment portion)
57b: projection
71: metallic-terminal-member retainer
S1, S2: dimension along longitudinal direction of element between rear end of electrode terminal and front end of chamfer

DETAILED DESCRIPTION OF THE PREFERRED EMBODIMENTS

The invention will next be described in detail with reference to the drawings. However, the present invention should not be construed as being limited thereto.

In the present mode, the invention is embodied as a full range air/fuel ratio sensor for detecting oxygen concentration in exhaust gas. Thus, the configuration of the sensor will first be described in detail.

In the drawings, reference numeral 1 denotes a full range air/fuel ratio sensor. A sensor element 21 is airtightly fixed in the interior of a tubular metallic shell body 11 (hereinafter, also referred to as the shell body 11). The sensor element 21 is formed predominantly of ceramic, has an elongated plate-like shape having a rectangular cross section, and includes a detection portion (not shown) 21a located at its front-end portion (a lower portion in the drawings) to be directed toward a measurement object. The metallic shell body 11 is formed into a stepped cylindrical shape such that its inside diameter concentrically increases in an upward direction. External threads 12 are formed at a lower end portion of the outer circumferential surface of the metallic shell body 11 and are used to fix the shell body 11 to an exhaust pipe of an engine. Fixation means for airtightly fixing the sensor element 21 is disposed inside the shell body 11 and outside the sensor element 21. The fixation means is configured as follows: a tubular member 30 is fitted into the shell body 11 such that its inward rim rests on an inner, lower stepped portion of the shell body 11; and a holder 31 formed of alumina, talc 32, and a sealing material (talc in the present embodiment) 33, from bottom to top, are disposed on the inward rim in the tubular member 30. A sleeve 35 is disposed on the sealing material 33. A thin-walled crimping cylindrical portion 16 integral with a cylindrical portion 15 located at a rear end portion of the shell body 11 is bent inward and compressed frontward so as to compress the inner sealing materials 32 and 33 and the like via a ring washer 36, thereby airtightly fixing the element 21 in the interior of the metallic shell body 11. A rectangular hole whose shape as viewed from the direction of an axis G corresponds to a cross-sectional shape of the element 21 is formed in the sleeve 35 and the like at a radially inward center and is used to coaxially fix the sensor element 21 in the shell body 11.

The thus-fixed element 21 is such that a front end portion (a lower end portion in FIG. 1) where the detection portion 21a is located projects by a predetermined amount (length) from the front end of the shell body 11 and such that a rear end portion projects by a predetermined amount (length) from the rear end of the sleeve 35. In the present embodiment, a protector (protection cover) 18 in which a plurality of holes are formed and which has a dual structure is fixed to the front end of the shell body 11 so as to surround a front end portion (detection portion 21a) of the element 21 projecting from the front end of the shell body 11. A large-diameter portion 19 projecting radially outward is formed on the shell body 11 at an intermediate portion with respect to the direction of the axis G. The large-diameter portion 19 is a polygonal portion to which a tool is fitted for screwing the external threads 12 of the shell body 11 so as to attach the sensor 1 to an exhaust pipe (not shown). A sealing gasket 20 is attached to the lower surface of the polygonal portion.

Figure 2A:
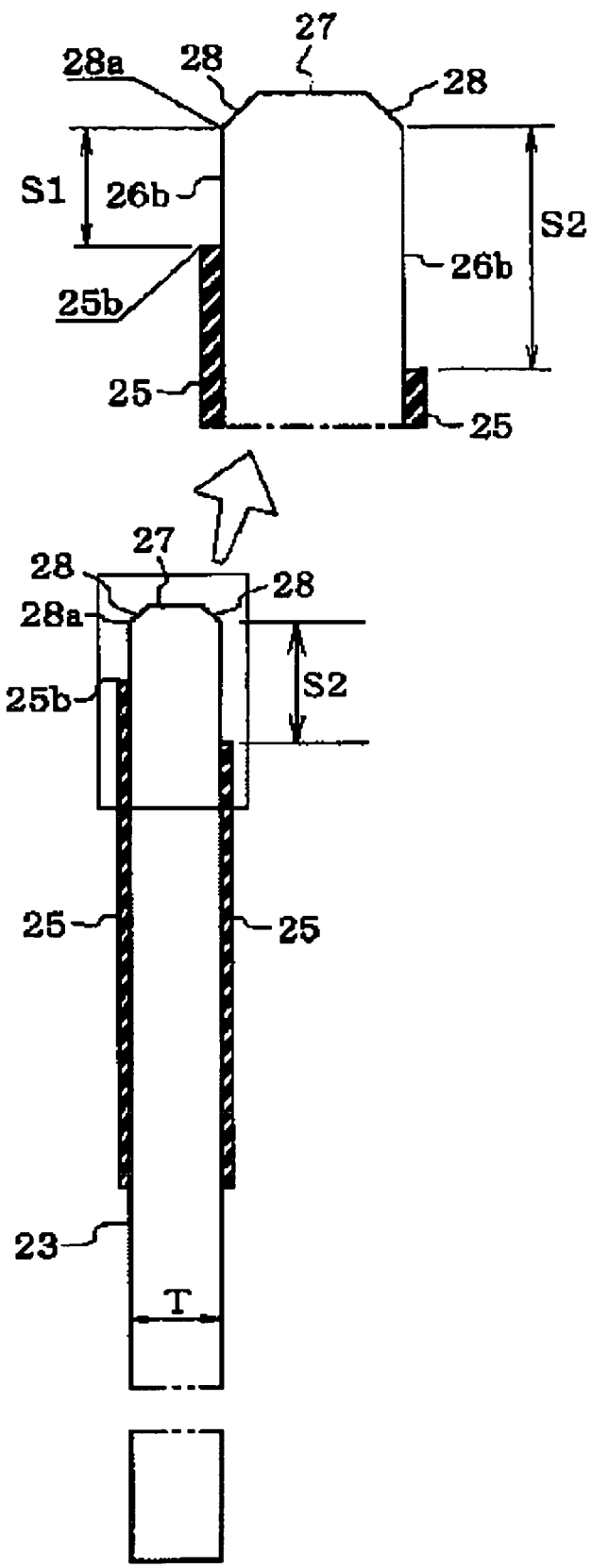
FIG. 2A is a side view.
Figure 2B:
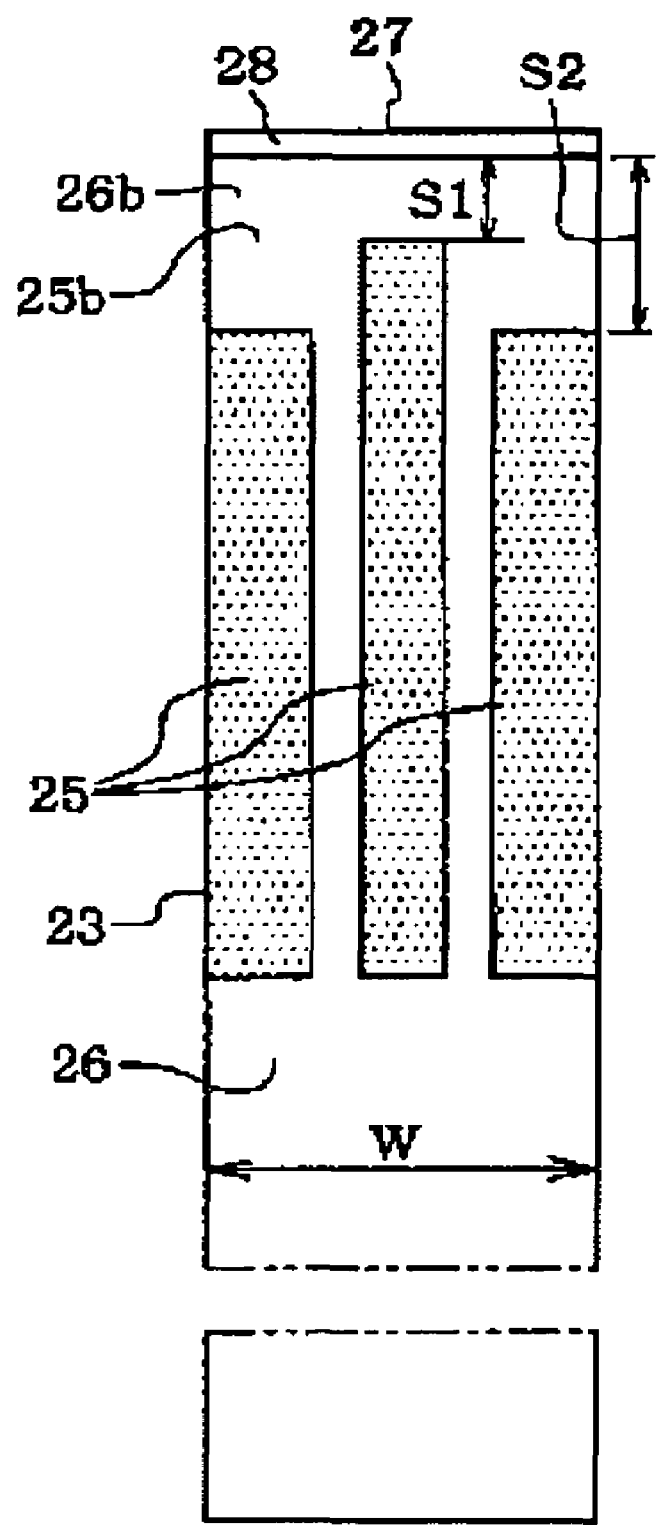
FIG. 2B is a left-hand view of FIG. 2A.
Figure 2C:
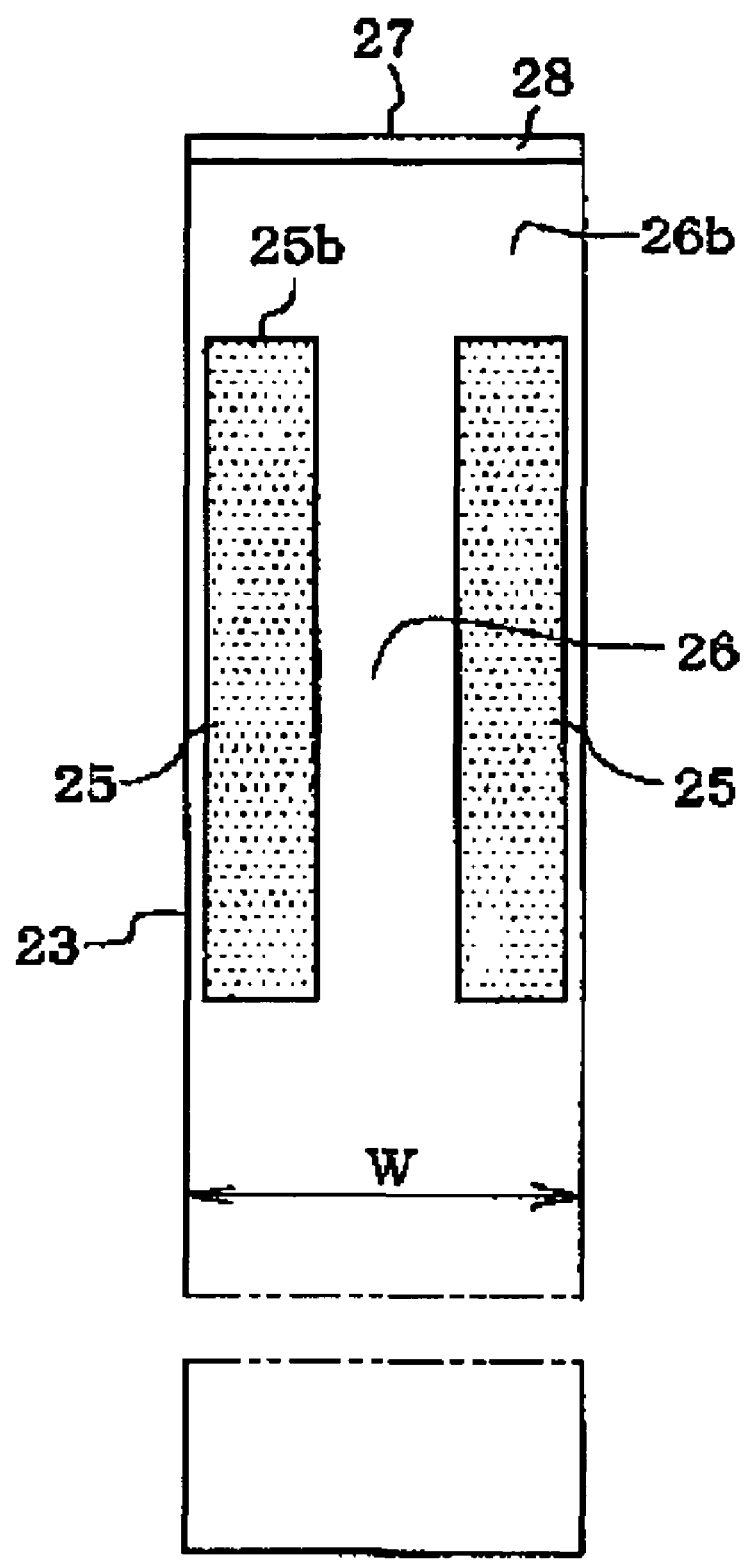
FIG. 2C is a right-hand view of FIG. 2A.

Next, the element 21 which is fixed in the shell body 11 as described above will be described in detail. As shown in FIGS. 2A to 2C, in the element 21 used in the present embodiment, three or two electrode terminals 25 are formed side by side on one of side surfaces (hereinafter, also referred to as surfaces) 26, which are wide surfaces, of a rear end portion 23 projecting from the sleeve 35. Since the element 21 used as a full range air/fuel ratio sensor is a conventionally known one, a detailed description of its internal structure or the like is omitted, but its schematic configuration is described below. First, the element 21 is formed by monolithic firing of an element portion and a heater portion. The element portion is configured such that an oxygen pump element and an oxygen concentration cell element are laminated via a spacer having a measuring chamber formed therein. The oxygen pump element is configured such that a pair of electrodes are formed on a solid electrolyte layer, and the oxygen concentration cell element is configured such that a pair of electrodes are formed on a solid electrolyte layer. The heater portion is configured such that a heating resistor is sandwiched between electrically insulative layers. The three electrode terminals 25 formed on one surface 26 are connected to corresponding electrodes of the element portion (one electrode terminal 25 is commonly connected to an electrode of the oxygen concentration cell element and an electrode of the oxygen pump element which faces the measuring chamber). The two electrode terminals 25 formed on the other surface 26 are connected to corresponding opposite ends of the heating resistor. Each of the electrode terminals 25 assumes a narrow elongated rectangular shape extending along the longitudinal direction of the element 21. The electrode terminals 25 are formed by simultaneously firing a green element of the element 21 and metallization paste applied by printing to the green element. The electrode terminals 25 are as thin as 10 mm to 30 mm and each assumes the form of a finely raised layer.

A chamfer 28 of, for example, a 45-degree bevel is formed on an edge of the element 21 defined by the rear end surface 27 and each of the wide surfaces 26 on which the electrode terminals 25 are formed. The chamfer 28 is of C0.1 (mm) to C0.5 (mm). The term "C0.1 to C0.5" means that the cut lengths of the two planes cut by the chamfer are 0.1 mm to 0.5 mm, respectively. A rear end 25b of the electrode terminal 25 is located so as to be biased by a dimension S1 (e.g., 1.1 mm) or a dimension S2 (e.g., 2.0 mm) along the longitudinal direction of the element 21 toward the front end of the element 21 from an end 28a of the chamfer 28 located on a side toward the front end of the element 21. The dimension S1 and the dimension S2 are longer than a dimension along the longitudinal direction between the rear end surface 27 of the element 21 and the end 28a of the chamfer 28. Thus, in the present embodiment, a flat surface 26b extending over a relatively long distance is present between the rear ends 25b of the electrode terminals 25 and the front ends 28a of the chamfers 28 located on a side toward the front end of the element 21. The sensor 1 of the present embodiment is manufactured by engaging a lower half assembly 101 in which the above-described element 21 is fixed in the shell body 11, and an upper half assembly 102 formed of other components, as will be described below (see FIG. 9).

Although unillustrated in detail, five lead wires 61 extend from the rear end, which is an upper end in the drawings, of the sensor 1 to the exterior of the sensor 1. Metallic terminal members 51 are crimped to corresponding core wires of distal ends of the lead wires 61 which are located in the sensor 1. The metallic terminal members 51 are disposed in a tubular metallic-terminal-member retainer 71 so as to pinch the rear end portion 23 of the element 21 by means of their own spring property. The tubular metallic-terminal-member retainer 71 is disposed in the shell body 11 and formed of an electrically insulative material. The metallic terminal members 51 are electrically connected to the corresponding electrode terminals 25 of the element 21 inserted into the metallic-terminal-member retainer 71. The metallic terminal members 51 and the metallic-terminal-member retainer 71 will be described in detail below. The metallic-terminal-member retainer 71 in which the metallic terminal members 51 are disposed is fixed as described below in the interior of an external tube 81 fixed to the shell body 11 and serving as a casing. An externally formed flange 73 of the metallic-terminal-member retainer 71 rests on a support ring 80 which is fixed at the inside of the external tube 81. An elastic sealing material (rubber) 85 through which the lead wires 61 extend is disposed on the upper end of the metallic-terminal-member retainer 71, so that the front end surface of the elastic sealing material 85 abuts the upper end of the metallic-terminal-member retainer 71. By means of compressing, in a diameter-reducing manner, a small-diameter tube portion 83 located at an upper end portion of the external tube 81, the elastic sealing material 85 seals a rear end portion of the sensor 1 and is fixed in the external tube 81.

Next, the metallic terminal members 51 will be described in detail with reference to FIGS. 1 to 6. The present embodiment employs five metallic terminal members 51 so as to correspond to the lead wires 61. The metallic terminal members 51 have the same basic configuration. However, in the present embodiment, a wider material is used to form the metallic terminal members 51 which are connected to the corresponding two electrode terminals 25 formed on one side surface 26 (shown in FIG. 2C) of the element 21, whereas a narrower material is used to form the metallic terminal members 51 which are connected to the corresponding three electrode terminals 25 formed on the other side surface 26 (shown in FIG. 2B). In the present embodiment, among the metallic terminal members 51 to be pressed against the corresponding three electrode terminals 25 shown at left in FIG. 5, only the central metallic terminal member 51 assumes the shape shown in FIG. 4. Other metallic terminal members assume the shape shown in FIG. 3.

Figure 3:
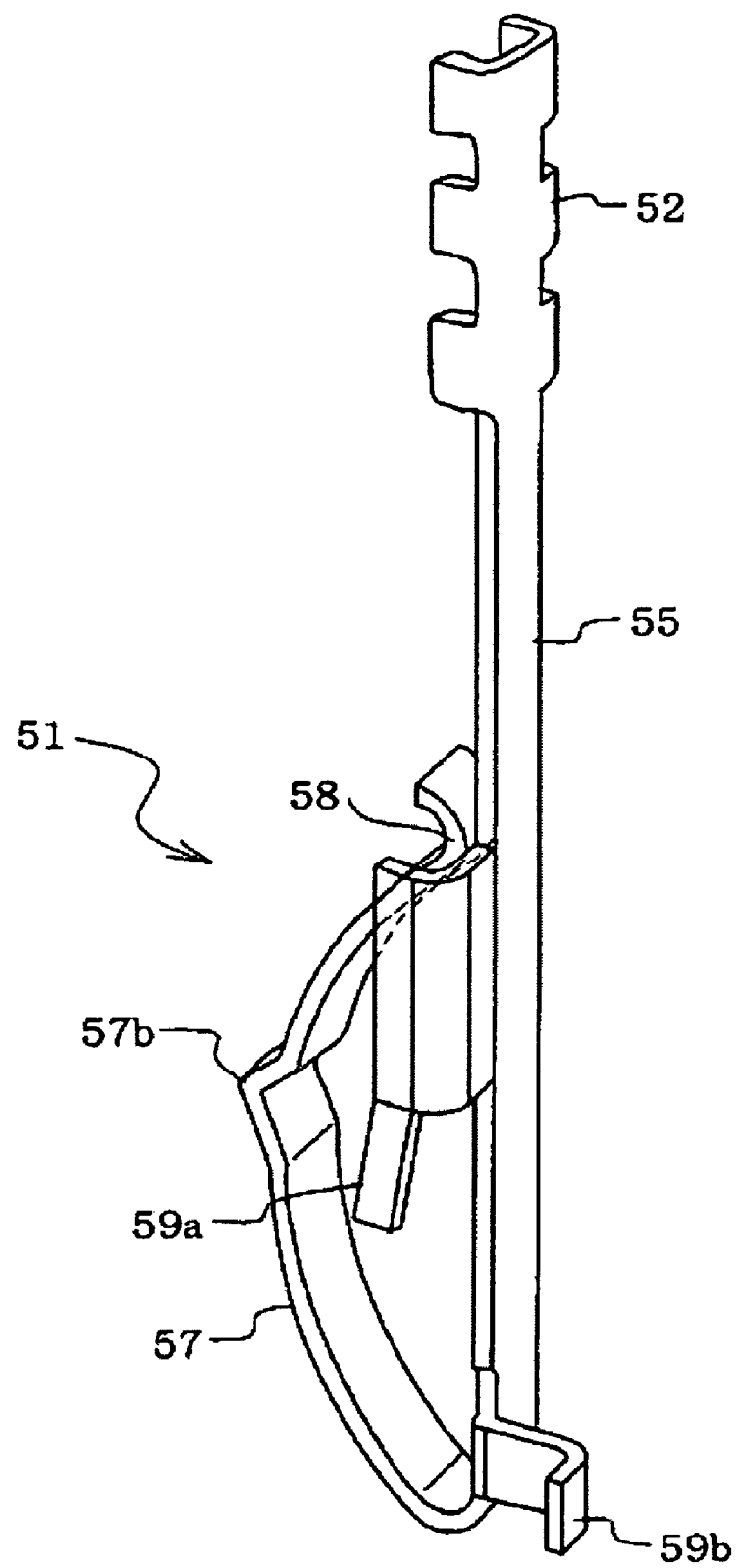
FIG. 3 is an enlarged view of a metallic terminal member.

Specifically, the metallic terminal member 51 shown in FIG. 3 is obtained by forming a blank having a predetermined shape from a metal (e.g., stainless steel) sheet having a spring property and by pressing the blank into a predetermined shape. A portion of the metallic terminal member 51 subsequent to the lead wire connection portion 52 crimped to a distal end (a portion of a core wire) of the lead wire 61 is formed as described below. A support portion 55 extends downward substantially straight from a front end of the lead wire connection portion 52. A portion extending from a front end of the support portion 55 is bent at the front end of the support portion 55 in a turnback fashion toward the element 21 and the corresponding electrode terminal 25 and is curved into a curved portion 57 which arcuately projects toward the element 21. A turnback end portion 58 of the curved portion 57 abuts an intermediate portion of the support portion 55 and is thereby supported by the support portion 55. In the metallic terminal member 51, an intermediate portion of the curved portion 57 serves as a portion (electrode connection portion) to be pressed against the corresponding electrode terminal 25 of the element 21 and is formed into a projection 57b which is V-shaped and projects toward the corresponding electrode terminal 25. A lateral-shift prevention spring 59a is formed at one side of the support portion 55 in order to prevent a lateral shift of the metallic terminal member 51 in the metallic-terminal-member retainer 71. A positioning hook 59b is formed at one side of the front end of the support portion 55.

In the case of the metallic terminal member 51 shown in FIG. 4, a portion subsequent to the lead wire connection portion 52 crimped to a distal end (a portion of a core wire) of the lead wire 61 is formed as described below. An intermediate portion 53 extends downward substantially straight from a front end of the lead wire connection portion 52. A support portion 55 extends from the intermediate portion 53 in the following manner: about ¼ thereof is arcuately bent at 54 toward a side opposite the element 21 at the front end of the intermediate portion 53, and the remaining portion extends downward substantially straight. A portion extending from a front end of the support portion 55 is bent at the front end of the support portion 55 in a turnback fashion toward the element 21 and the corresponding electrode terminal 25 and is curved into a curved portion 57 which arcuately projects toward the element 21. A turnback end portion 58 of the curved portion 57 abuts the support portion 55 and is thereby supported by the support portion 55. An intermediate portion of the curved portion 57 serves as a portion (electrode connection portion) to be pressed against the corresponding electrode terminal 25 of the element 21 and is formed into a projection 57b which is V-shaped and projects toward the corresponding electrode terminal 25. In the metallic terminal member 51 of FIG. 4, the metallic-terminal-member retainer 71 supports the support portion 55 from both sides thereof, so that a portion subject to lateral sliding is hardly present. Thus, the lateral-shift prevention spring 59a shown in FIG. 3 is not needed. However, the positioning hook 59b is formed at opposite sides of the front end of the support portion 55.

Figure 4:
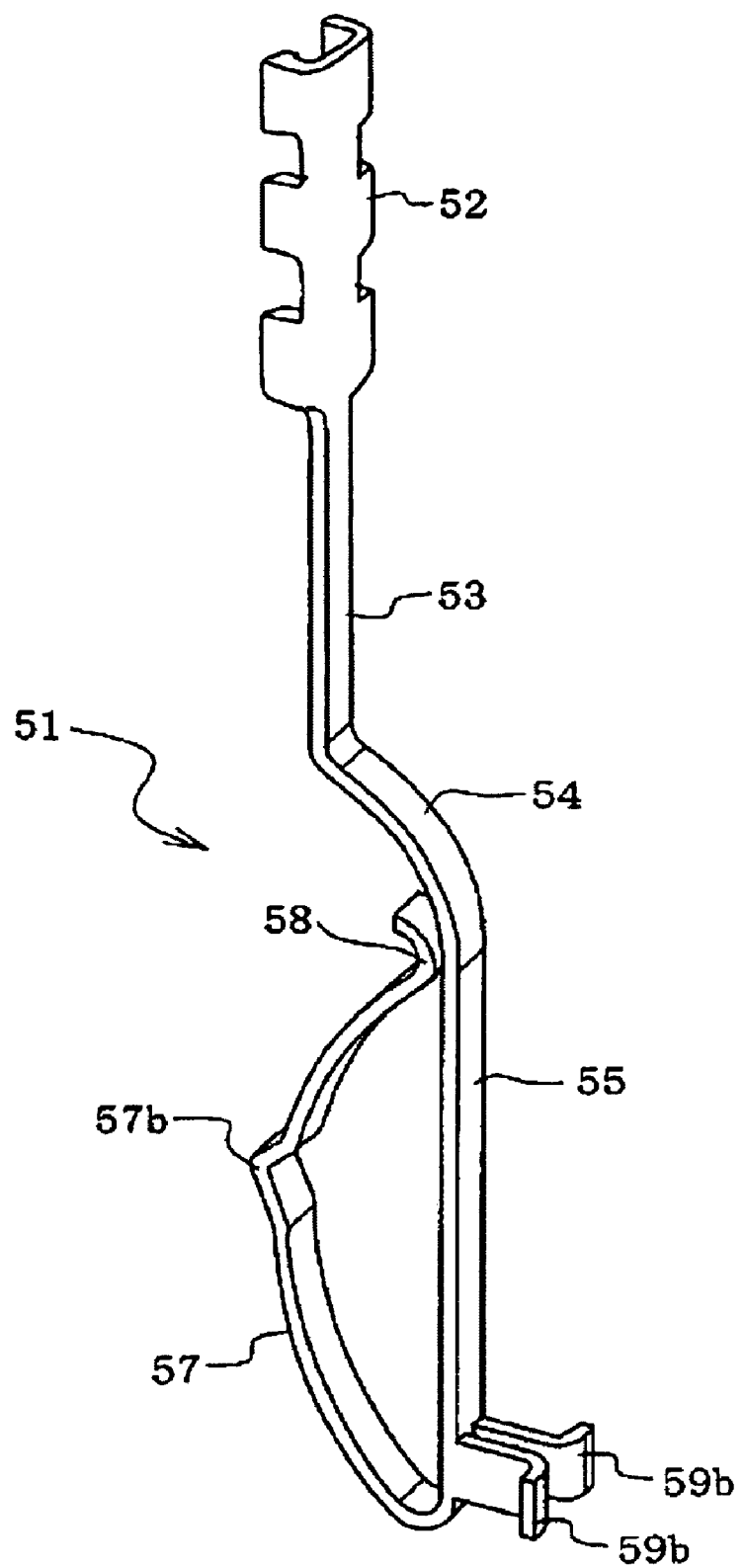
FIG. 4 is an enlarged view of a metallic terminal member.
Figure 5:
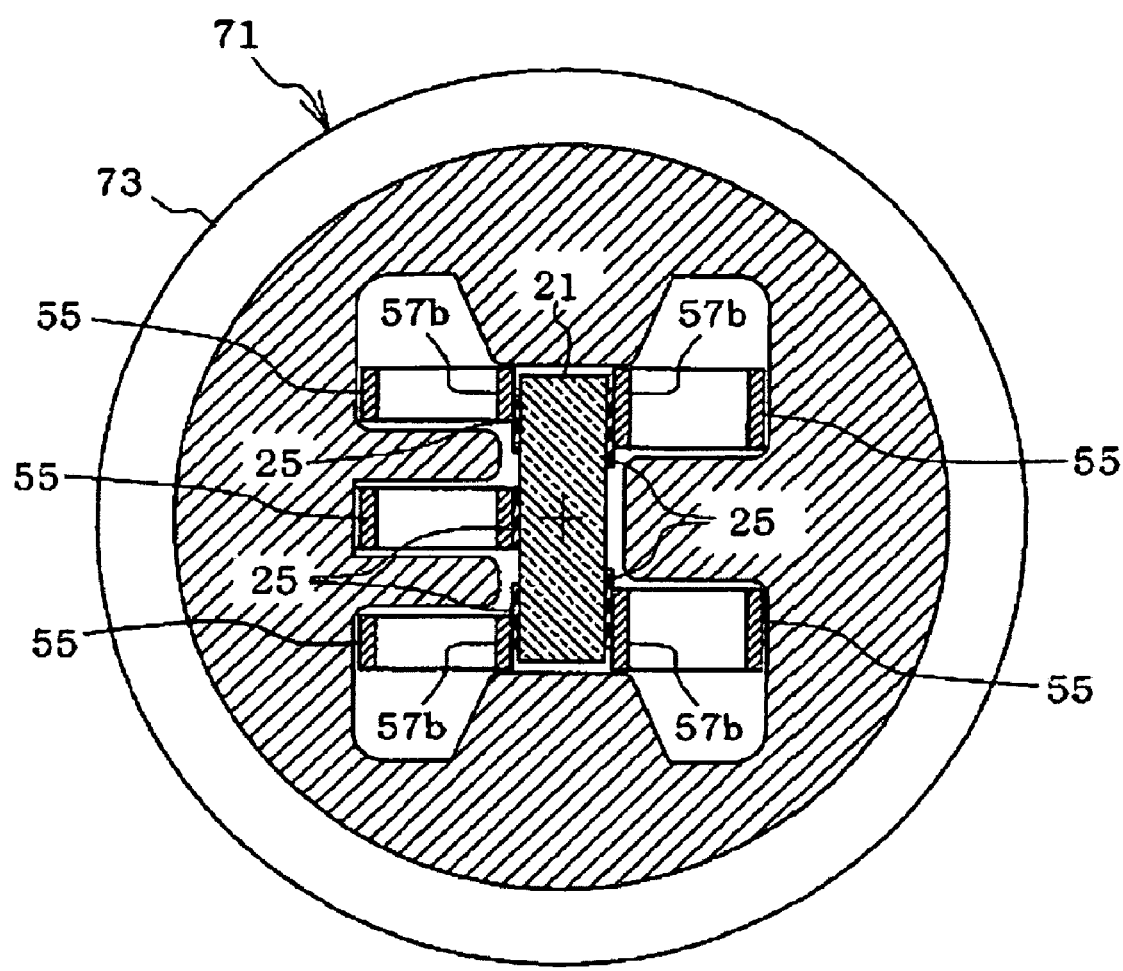
FIG. 5 is an enlarged cross-sectional view taken along line A-A of FIG. 1.
Figure 6:
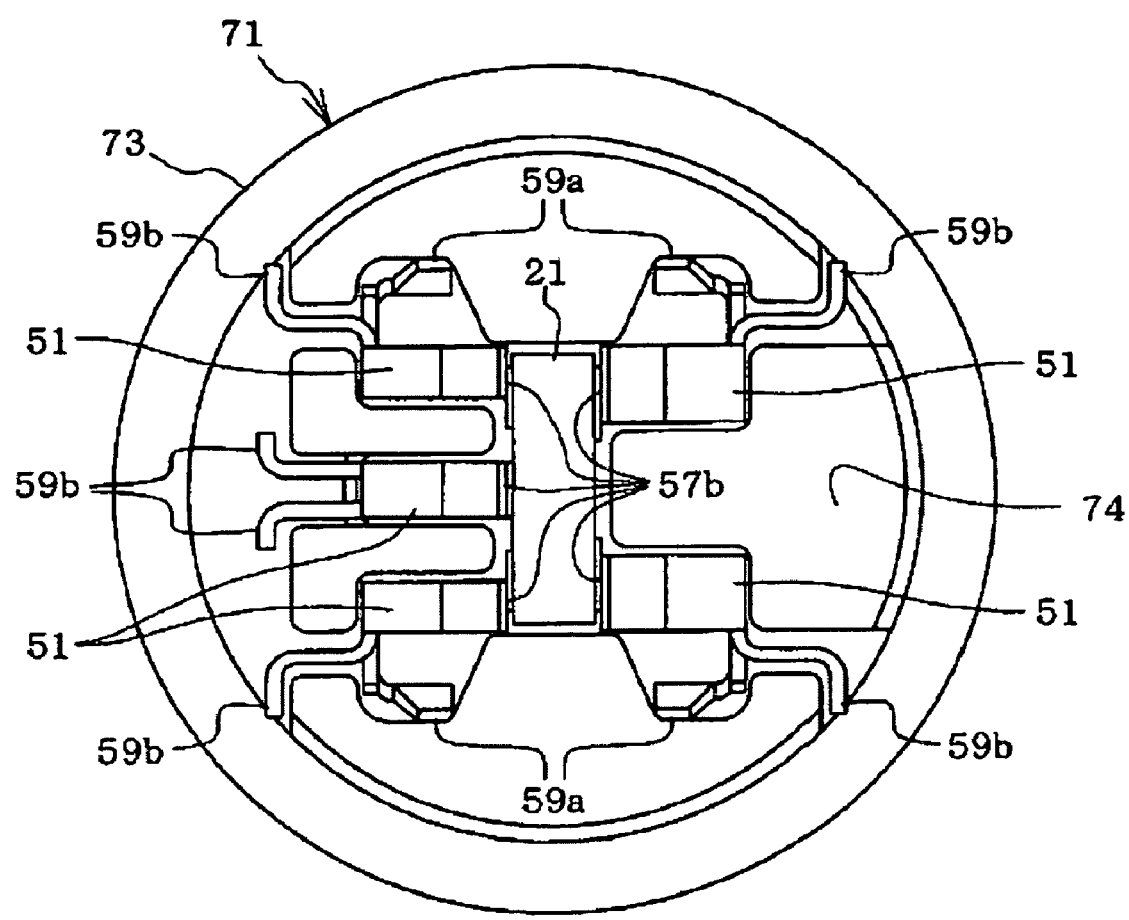
FIG. 6 is an enlarged view of a front end of a metallic-terminal-member retainer in which the metallic terminal members are disposed.

Notably, in the metallic terminal members 51 shown in FIGS. 3 and 4, the curved portion 57 and the end portion 58 correspond to the "turnback portion" and "abutment portion," respectively.

As shown in FIG. 1, in a condition where the thus-formed metallic terminal members 51 are incorporated in the sensor 1, the curved portions 57, which serve as electrode connection portions, of the mutually facing metallic terminal members 51 pinch therebetween the rear end portion 23 of the element 21 by means of their spring property, and the projections 57b of the metallic terminal members 51 are pressed against the corresponding electrode terminals 25, whereby the metallic terminal members 51 are electrically connected to the corresponding electrode terminals 25. In a condition where the metallic terminal members 51 are incorporated in the sensor 1 and are pressed against the corresponding electrode terminals 25 of the element 21 for electrical connection, the projections 57b are pressed outward, so that the curved portions 57 are elastically deformed in a compressive manner in a lateral direction in the metallic-terminal-member retainer 71. However, as shown in an upper drawing in FIG. 9, before assembly; i.e., before insertion of the element 21 (when the metallic terminal members are in a free condition), the curved portions 57 of the right and left metallic terminal members 51 project inward to a considerable extent, or the facing projections 57b press against each other. In each of the metallic terminal members 51 in a free condition, the end portion 58 located at a rear end portion of the curved portion 57 is separated from the support portion 55, since the curved portion 57 is not elastically deformed. The curved portion 57 is in a one-point support condition where its front end is integral with the front end of the support portion 55. Although a detailed description will be given below, when the element 21 is inserted from its rear end 27 between the inwardly projecting curved portions 57 of the mutually facing right and left metallic terminal members 51, the portions 57 being disposed within the metallic-terminal-member retainer 71, the inserted element 21 causes the mutually facing curved portions 57 of the metallic terminal members 51 to be elastically deformed so as to be outwardly spread. This in turn establishes electrical connection between the metallic terminal members 51 and the corresponding electrode terminals 25 of the element 21.

Figure 7:
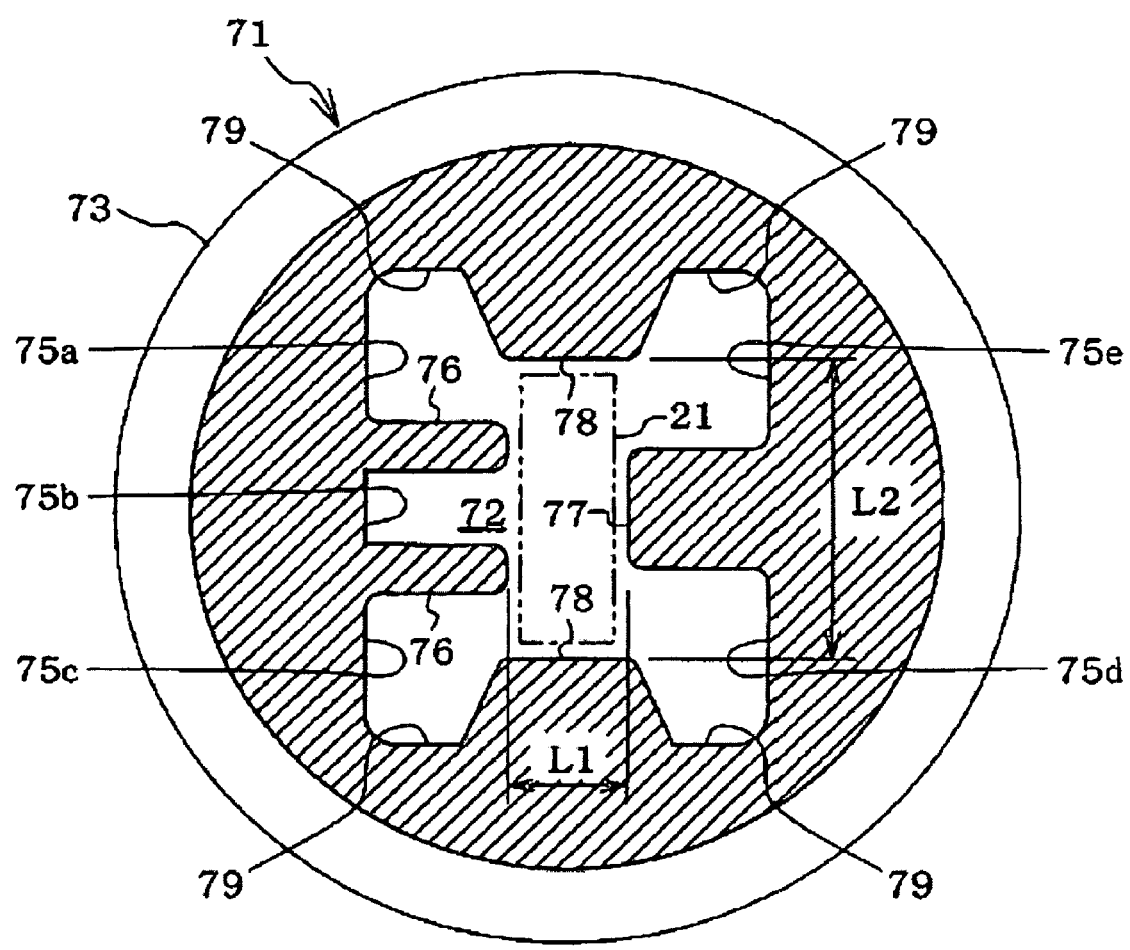
FIG. 7 is a cross-sectional view of the metallic-terminal-member retainer, showing a state of FIG. 5 with the metallic terminal members removed.
Figure 8:
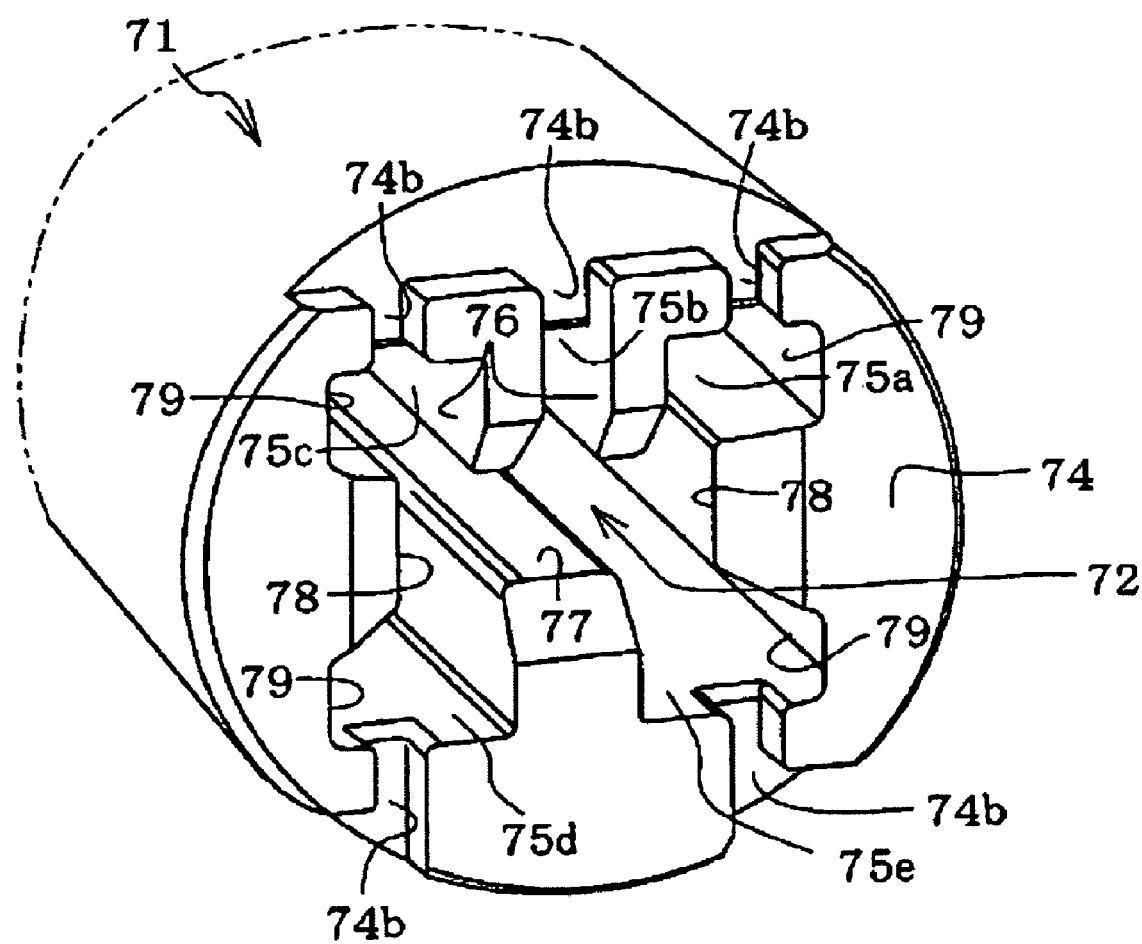
FIG. 8 is an enlarged perspective view of a front end of the metallic-terminal-member retainer.

Before describing in detail the metallic-terminal-member retainer 71 having the above-described metallic terminal members 51 disposed therein and a condition where the metallic terminal members 51 are disposed therein, the structure, shape, and the like of the metallic-terminal-member retainer 71 will be described in detail. In the present embodiment, the metallic-terminal-member retainer 71 is formed of alumina and assumes a cylindrical shape. The metallic-terminal-member retainer 71 has the above-mentioned flange 73 formed on the exterior thereof. As shown in FIG. 7, an element insertion hole 72 and metallic-terminal-member insertion grooves 75a to 75e are formed in the metallic-terminal-member retainer 71 at the center on a cross section so as to extend along the axis G of the sensor 1. The element 21 can be inserted along its longitudinal direction into the element insertion hole 72. The metallic terminal members 51 are inserted into the corresponding metallic-terminal-member insertion grooves 75a to 75e and are arranged at the right and the left of the element insertion hole 72. The three metallic-terminal-member insertion grooves 75a to 75c are provided on one side (at the left in FIG. 7), and the two metallic-terminal-member insertion grooves 75d and 75e are provided on the other side. The metallic-terminal-member insertion grooves 75a to 75e accommodate the corresponding metallic terminal members 51 along the axial direction such that the curved portions 57 face inward (on a side toward the axis). An insulative partition wall (insulation rib) 76 extending along the axis G is formed between the grooves 75a to 75c so that the metallic terminal members 51 are arranged while electrical insulation is established therebetween. An insulative partition wall (insulation rib) 77 extending along the axis is formed between the grooves 75d and 75e so that the metallic terminal members 51 are arranged while electrical insulation is established therebetween. A dimension L1 as measured on the cross section (FIG. 7) between the end surfaces of the mutually facing partition walls 76 and 77 is set slightly greater than a thickness T of the element 21. Elongated projections 78 extending along the axis G and having a trapezoidal cross section are formed in a region of the element insertion hole 72 which corresponds to the thickness of the element 21. A dimension L2 between the mutually facing elongated projections 78 is set slightly greater than a width W of the element 21. Portions of the metallic-terminal-member insertion grooves which correspond to side portions of the elongated projections 78 are formed into respective recesses 79 into which the corresponding lateral-shift prevention springs 59a of the metallic terminal members 51 are fitted. Engagement recesses 74b are formed in a notch-like fashion on a front end surface 74 of the metallic-terminal-member retainer 71 (see FIG. 8). The hooks 59b formed at front-end portions of the metallic terminal members 51 are fitted into the corresponding engagement recesses 74b.

The metallic terminal members 51 whose lead wire connection portions 52 are crimped to the corresponding distal ends of the lead wires 61 are inserted frontward into the corresponding metallic-terminal-member insertion grooves 75a to 75c of the metallic-terminal-member retainer 71 from the rear end (upper end in FIG. 1) of the retainer 71. The hooks 59b located at the front ends of the metallic terminal members 51 are fitted into the corresponding engagement recesses 74b formed at the front end 74 of the retainer 71. Then, the lead wires 61 are pulled rearward. By this procedure, the metallic terminal members 51 are disposed in place in the metallic-terminal-member retainer 71 while electrical insulation is established therebetween. At this stage (when the metallic terminal members 51 are in a free condition), the curved portions 57 of the right and left metallic terminal members 51 project inward such that a gap between the mutually facing, inwardly projecting curved portions 57 of the right and left metallic terminal members 51 is smaller than the thickness of the element 21 or such that the mutually facing curved portions 57 press against each other (see FIG. 9). The lead wires 61 connected to the metallic terminal members 51 are passed through the uncompressed elastic sealing material (rubber) 85 in advance, and the elastic sealing material 85 is placed on the upper end of the metallic-terminal-member retainer 71. The support ring 80 is externally fitted to the metallic-terminal-member retainer 71 from the front end of the retainer 71 such that the support ring 80 abuts the flange 73. The external tube 81 is externally fitted to this assembly from above in the drawing. An intermediate portion of the external tube 81 is squeezed so as to squeeze an outer portion of the support ring 80 located inside of the external tube 81, whereby the metallic-terminal-member retainer 71 is fixed in the external tube 81 so that its frontward movement is restricted.

Figure 9:
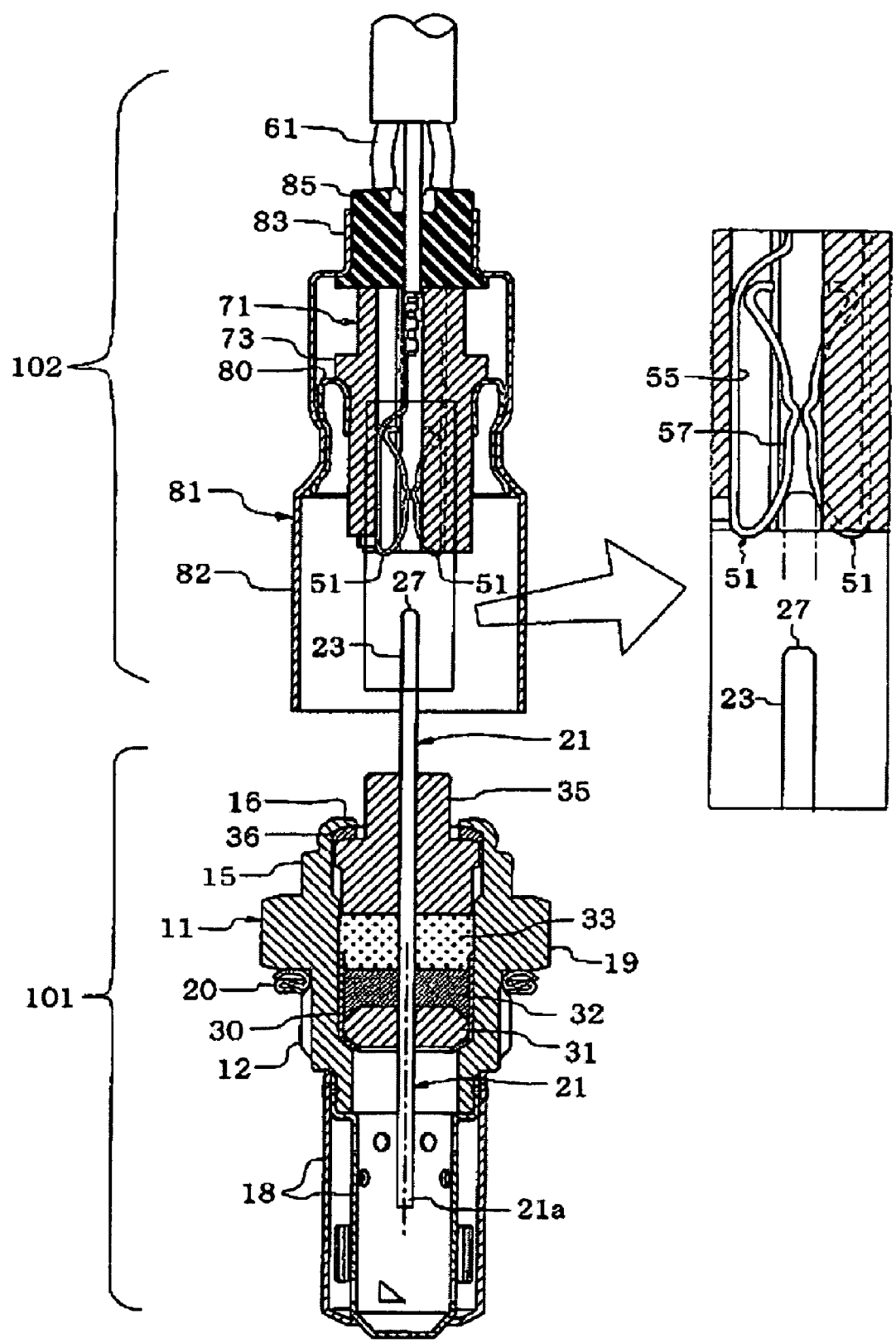
FIG. 9 is a longitudinal sectional view illustrating assembly of the sensor of FIG. 1, and an enlarged view of essential portions of the sensor.

The upper half assembly 102 composed of the metallic-terminal-member retainer 71, the metallic terminal members 51, the external tube 81, and the like is thus obtained. Subsequently, as shown in FIG. 9, the half assembly 102 and the previously described lower half assembly 101 are disposed coaxially. The rear end portion 23 of the element 21 projecting from the lower half assembly 101 is inserted, through relative movement, between the mutually facing metallic terminal members 51 in the metallic-terminal-member retainer 71, which retains therein a plurality of the metallic terminal members 51 while establishing electrical insulation between the metallic terminal members 51. At this time, the metallic terminal members 51 are disposed in place in the metallic-terminal-member retainer 71 such that, in a free condition (before insertion of the element), a gap smaller than the thickness of the element 21 is present between the inwardly projecting, mutually facing curved portions 57, or the mutually facing curved portions 57 press against each other. However, the mutually facing curved portions 57 fan out in a frontward direction and thus serve as a guide for insertion at the beginning of insertion of the rear end 27 of the element 21. When the rear end portion 23 of the element 21 is inserted between the mutually facing curved portions 57 of the metallic terminal members 51 disposed in the metallic-terminal-member retainer 71, the mutually facing curved portions 57 of the metallic terminal members 51 are elastically deformed so as to be outwardly spread and are pressed against and connected to the corresponding electrode terminals 25 formed on the side surfaces of the sensor element 21. Insertion of the element 21 causes the curved portions 57 of the metallic terminal members 51 to elastically deform such that their end portions 58 abut the corresponding support portions 55. After completing engagement of the metallic terminal members 51 with the element 21, the curved portions 57 of the metallic terminal members 51 are in a two-point support condition where the curved portions 57 are supported at two points by the respective support portions 55, so that the curved portions 57 can be firmly pressed against the corresponding electrode terminals 25 of the element 21, thereby establishing a stably connected condition.

After insertion, the front end of the external tube 81 is externally fitted to the cylindrical portion 15 located at a rear end portion of the metallic shell body 11. A front end portion of a large-diameter tube portion 82 is crimped radially inward against the cylindrical portion 15 of the metallic shell body 11. A portion of the external tube 81 which surrounds the elastic sealing material 85 is crimped radially inward, whereby the elastic sealing material 85 is compressively deformed and fixed to the external tube 81. At this time, the metallic-terminal-member retainer 71 is held between the elastic sealing material 85 and the support ring 80, thereby being held in the external tube 81. Next, full-arc laser welding is performed on the crimped portion where the front end portion of the large-diameter tube portion 82 and the cylindrical portion 15 of the metallic shell body 11 are crimped together, thereby yielding the sensor of FIG. 1.

Figure 10A:
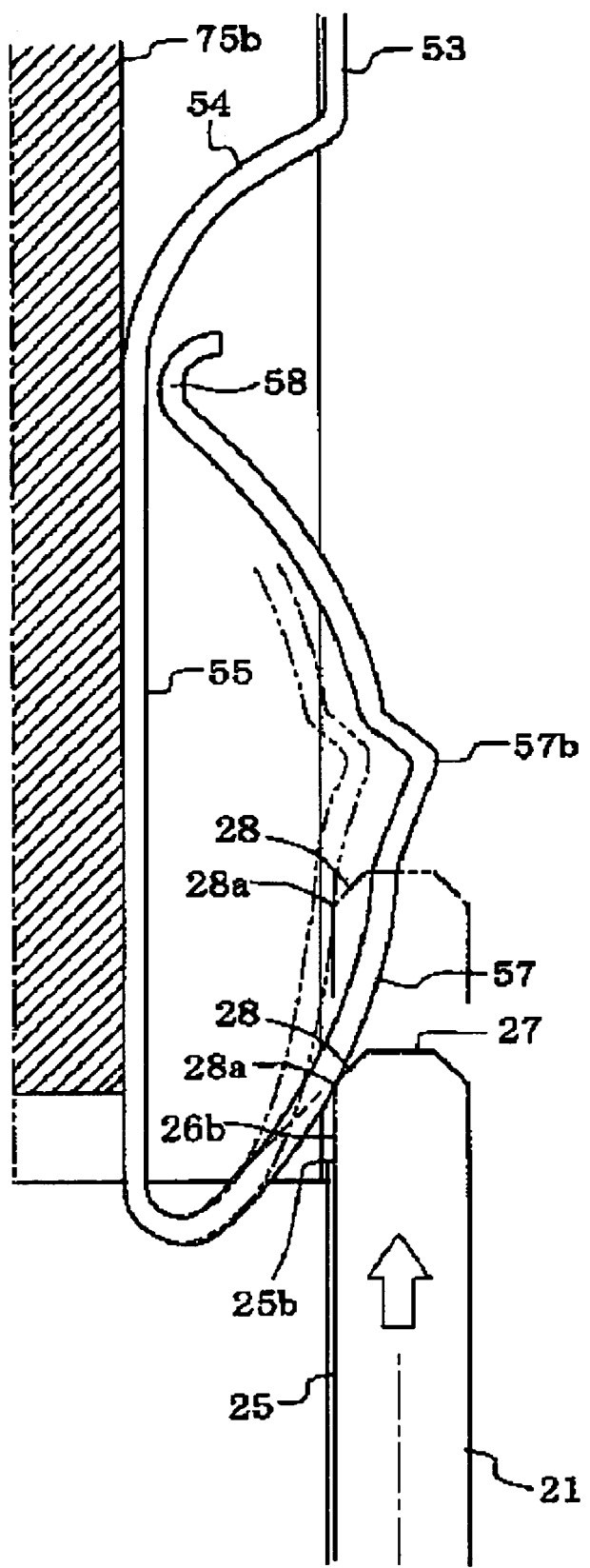
FIG. 10A is an enlarged view for illustrating insertion of the element.

As mentioned previously, in the element 21 to be inserted, the chamfer 28 is formed on an edge defined by the rear end surface 27 and each of the side surfaces 26 on which the electrode terminals 25 are formed; the rear ends 25b of the electrode terminals 25 located on the side toward the rear end of the element 21 are biased from the chamfers 28 toward the front end of the element 21; and the flat surface 26b is present between the rear ends 25b of the electrode terminals 25 and the front end 28a of each chamfer 28 located on the side toward the front end of the element 21. Meanwhile, upon inserting the rear end portion 23 of the element 21, as shown in FIG. 10A, insertion resistance increases when each of the chamfers 28 hits against the curved portions 57 of the metallic terminal members 51, and then the curved portions 57 of the metallic terminal members 51 pass over the chamfer 28. A large force generated in association with the increase in insertion resistance is applied directly to the front end 28a of the chamfer 28. However, in the present embodiment, since the rear ends 25b of the electrode terminals 25 are not exposed at the front end 28a of the chamfer 28, the subject large force is not applied directly to the rear ends 25b of the electrode terminals 25. In other words, force from the metallic terminal members 51 is applied to the electrode terminals 25 after the metallic terminal members 51 which have passed over the chamfer 28 reach the flat surface 26b of the element 21; i.e., after the insertion resistance has greatly decreased. Because the force is greatly reduced, damage to or exfoliation of the electrode terminals 25 can be prevented.

Even though the present embodiment uses metallic terminal members of an intensive spring quality, damage to the electrode terminals 25 is prevented, so that a terminal connection structure having a highly reliable electrical connection is obtained. In the present embodiment, the projections 57b are formed at portions of the metallic terminal members 51 which come into contact with the corresponding electrode terminals 25. Accordingly, in the terminal connection structure in which the element 21 is inserted to thereby connect the metallic terminal members 51 to the corresponding electrode terminals 25, the thus-formed projections 57b abut the corresponding electrode terminals 25 of the element 21 locally or in a concentrated manner. Thus, the contact surface pressure is increased, thereby enhancing the stability or reliability of electrical connection.

Figure 10B:
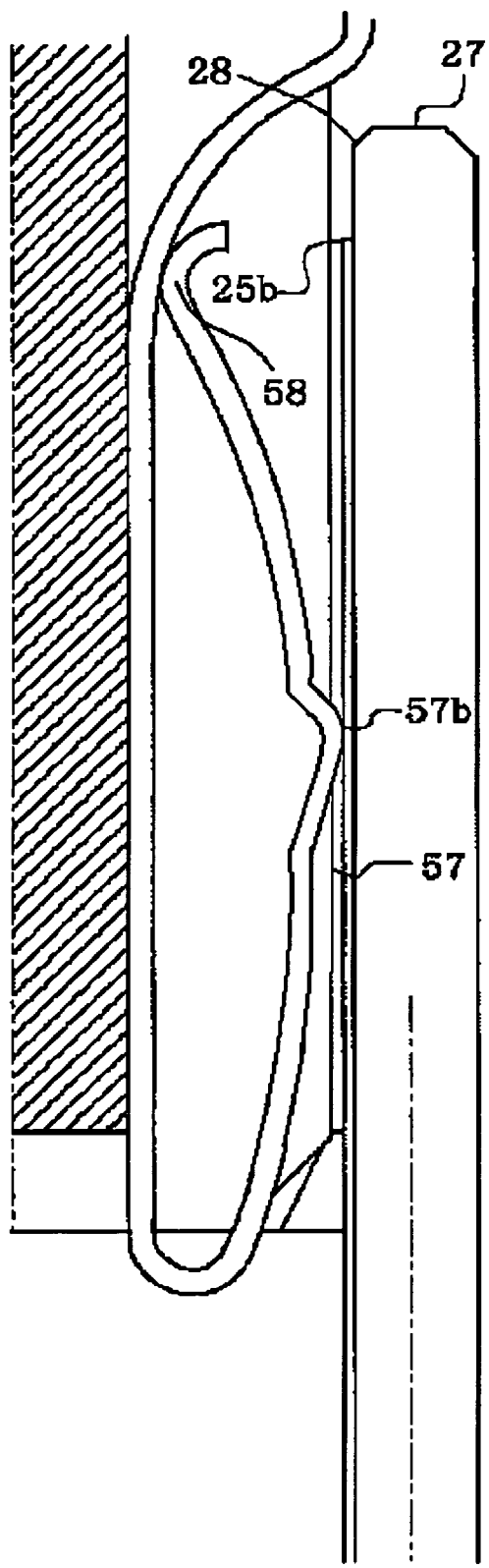
FIG. 10B is an enlarged view for illustrating the element after insertion.

Furthermore, in the present embodiment, the dimension of chamfering and the shape and dimensions of the metallic terminal members are appropriately adjusted such that, during engagement of the metallic terminal members 51 with the element 21 by means of moving the metallic terminal members 51 from the rear end of the element 21 toward the front end of the element 21, the end portions 58 of the curved portions 57 do not come into contact with the corresponding support portions 55 until the front ends of the curved portions 57 of the metallic terminal members 21 are moved frontward beyond the front ends of the chamfers 28 of the element 21. As shown in FIGS. 10A to 10B, the metallic terminal members 51 are configured such that, after the front ends of the curved portions 57 are moved frontward beyond the front ends of the chamfers 28 of the element 21, the end portions 58 of the curved portions 57 abut the corresponding support portions 55, whereby the metallic terminal members 51 are engaged with the element 21 in such condition that the curved portions 57 are each supported at two points by the corresponding support portions 55. By virtue of the thus-configured metallic terminal members 51, in engagement of the metallic terminal members 51 and the element 21, the distance on the element 21 over which the curved portions 57 move when passing over the chamfers and beyond can be shortened while being supported at two points by the respective support portions 55. Accordingly, during engagement of the element 21 and the metallic terminal members 51 which can be firmly connected to the element 21 such that the curved portions 57 are each supported at two points by the corresponding support portions 55, damage to the electrode terminals 25 of the element 21 can be prevented while the aforementioned effect of forming the chamfers 28 on the element 21 is realized.

In the above-described embodiment, a chamfer of C0.1 to C0.5 is formed on an edge of the element 21 defined by the rear end surface 27 and each of the surfaces 26 on which the electrode terminals 25 are formed. However, the chamfering dimension can be modified as appropriate so long as insertion is facilitated. Also, chamfering is not necessarily at a 45-degree bevel. A chamfering bevel of an appropriate angle can be employed. In place of a bevel-type chamfer, an arcuate chamfer can also be employed.

In the above-described embodiment, the electrode terminals 25 of the element 21 are formed such that two electrode terminals 25 are provided on one side surface, whereas three electrode terminals 25 are provided on the other side surface. Needless to say, the present invention can be embodied independent of the number of the electrode terminals 25. The above embodiment is described while mentioning a structure in which the metallic terminal members disposed on the opposite sides of the element pinch the element from both sides (at side surfaces). However, the present invention is not limited thereto. For example, the electrode terminals can be formed only on one side surface (single side) of the element.

Figure 11:
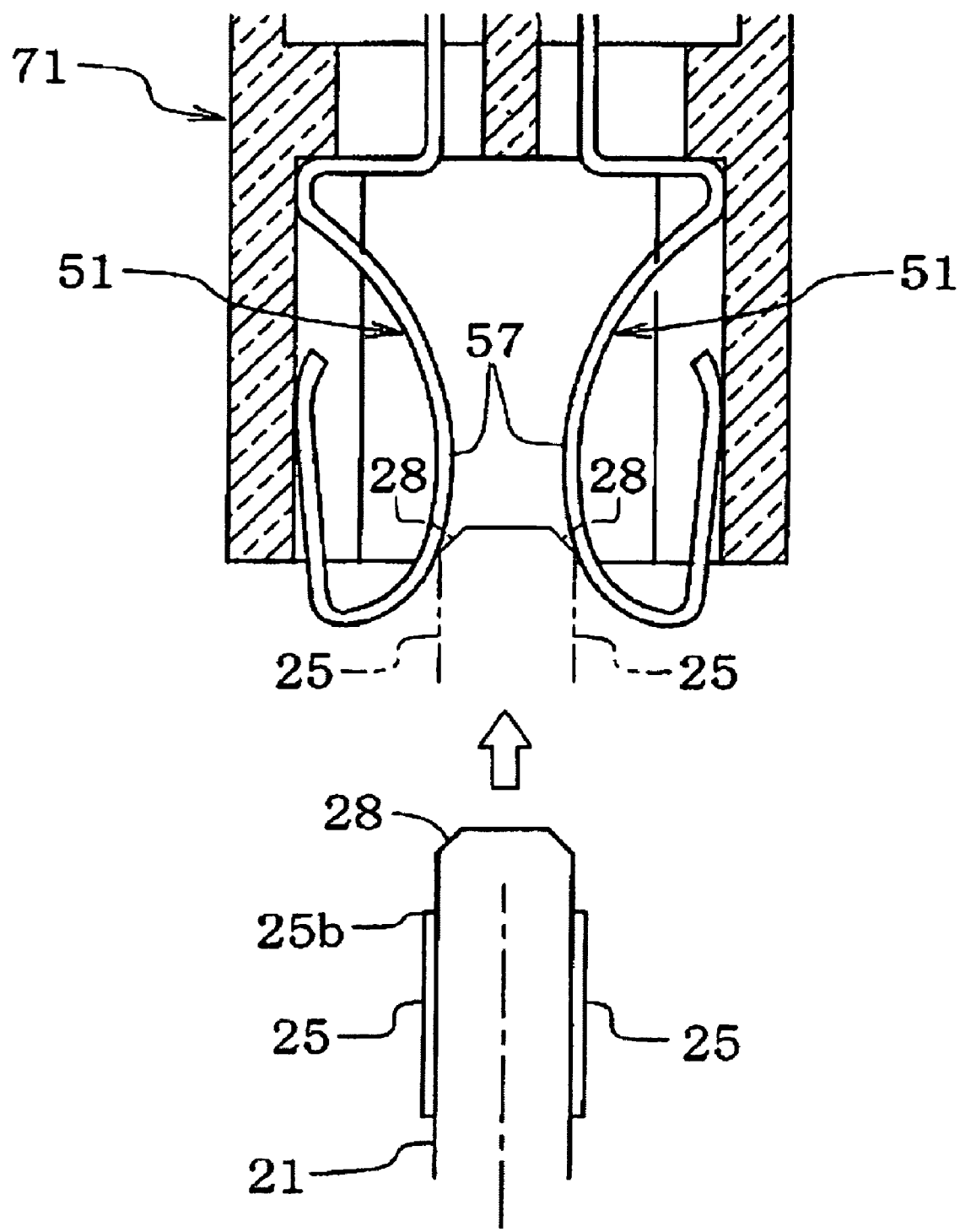
FIG. 11 is an enlarged view of essential portions of another embodiment.
Figure 12A:
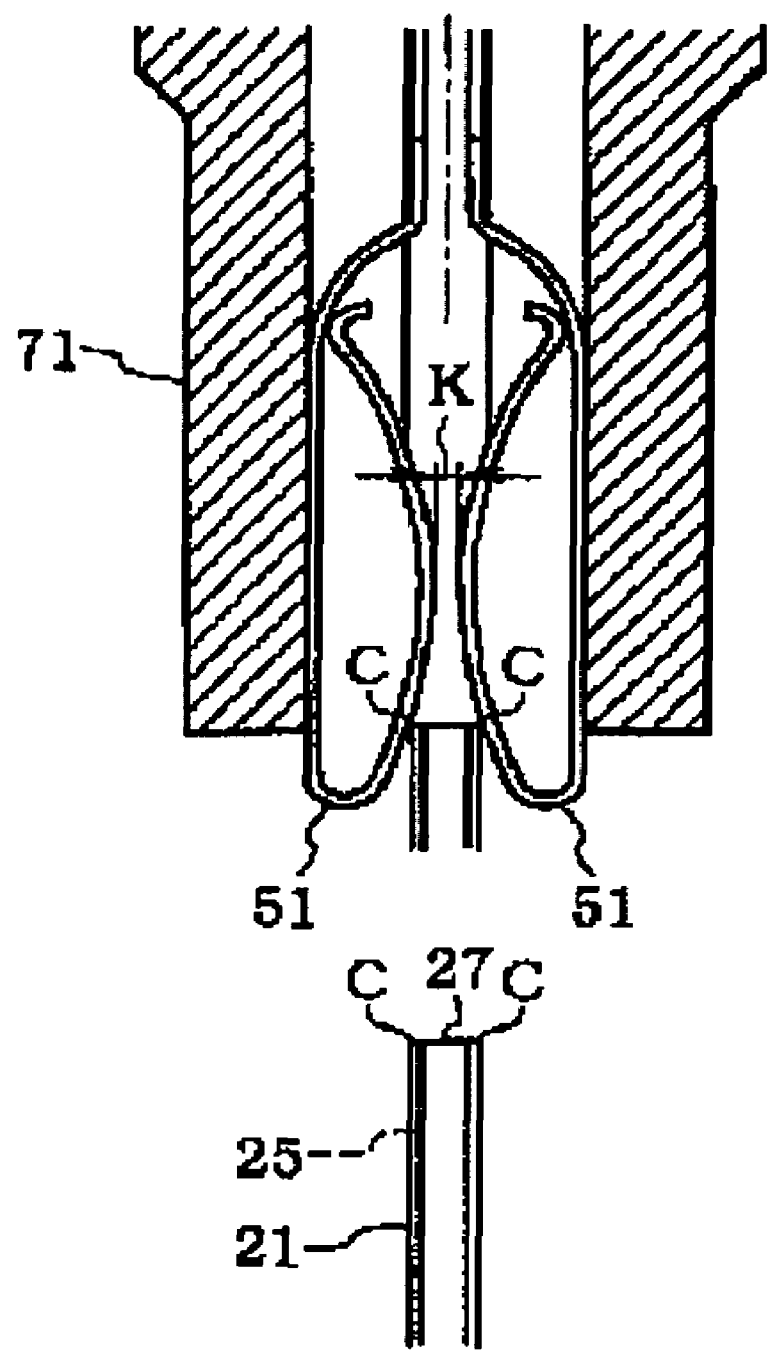
FIG. 12A is a view illustrating insertion of an element in a conventional terminal connection structure.
Figure 12B:
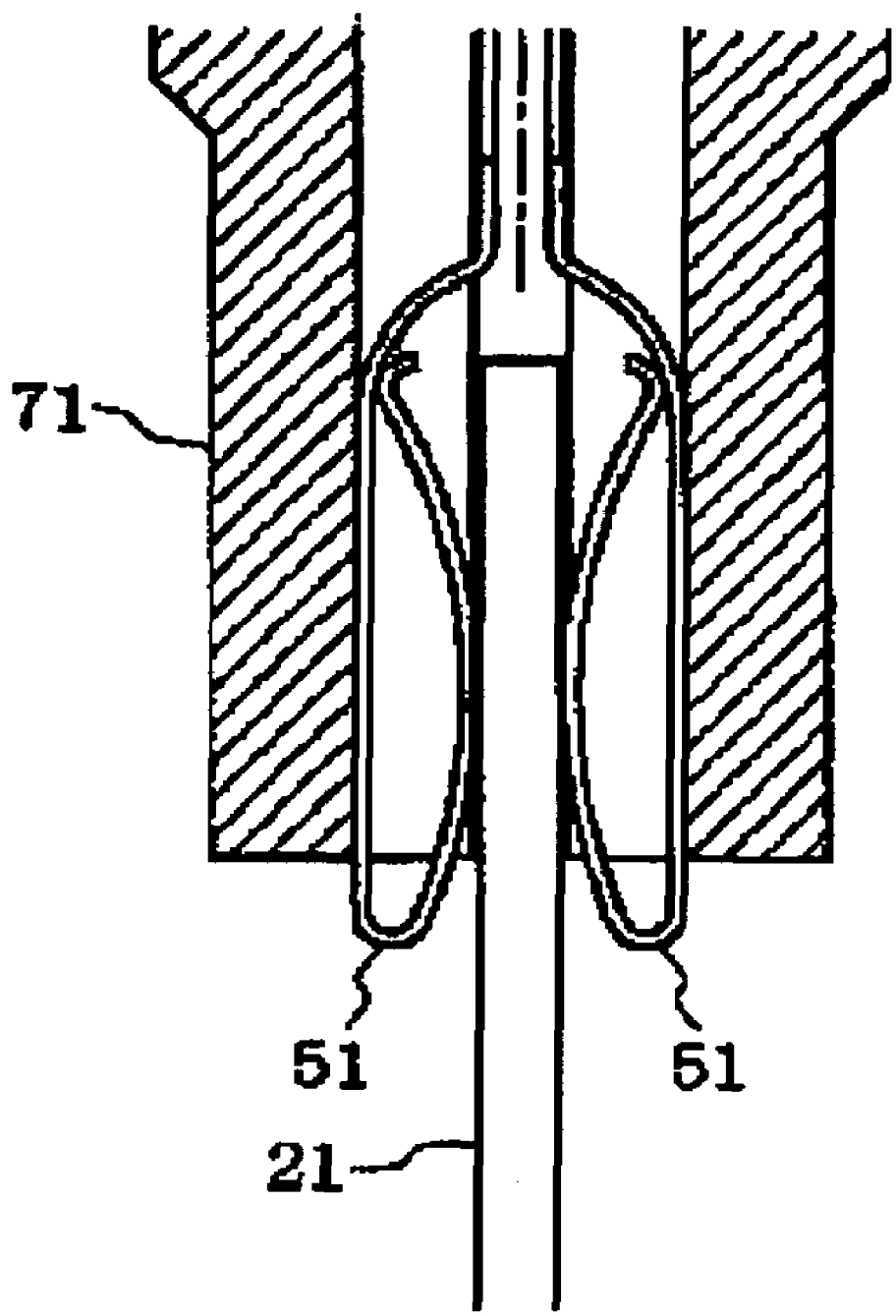
FIG. 12B is a view illustrating an element after insertion in a conventional terminal connection structure.
Figure 13:
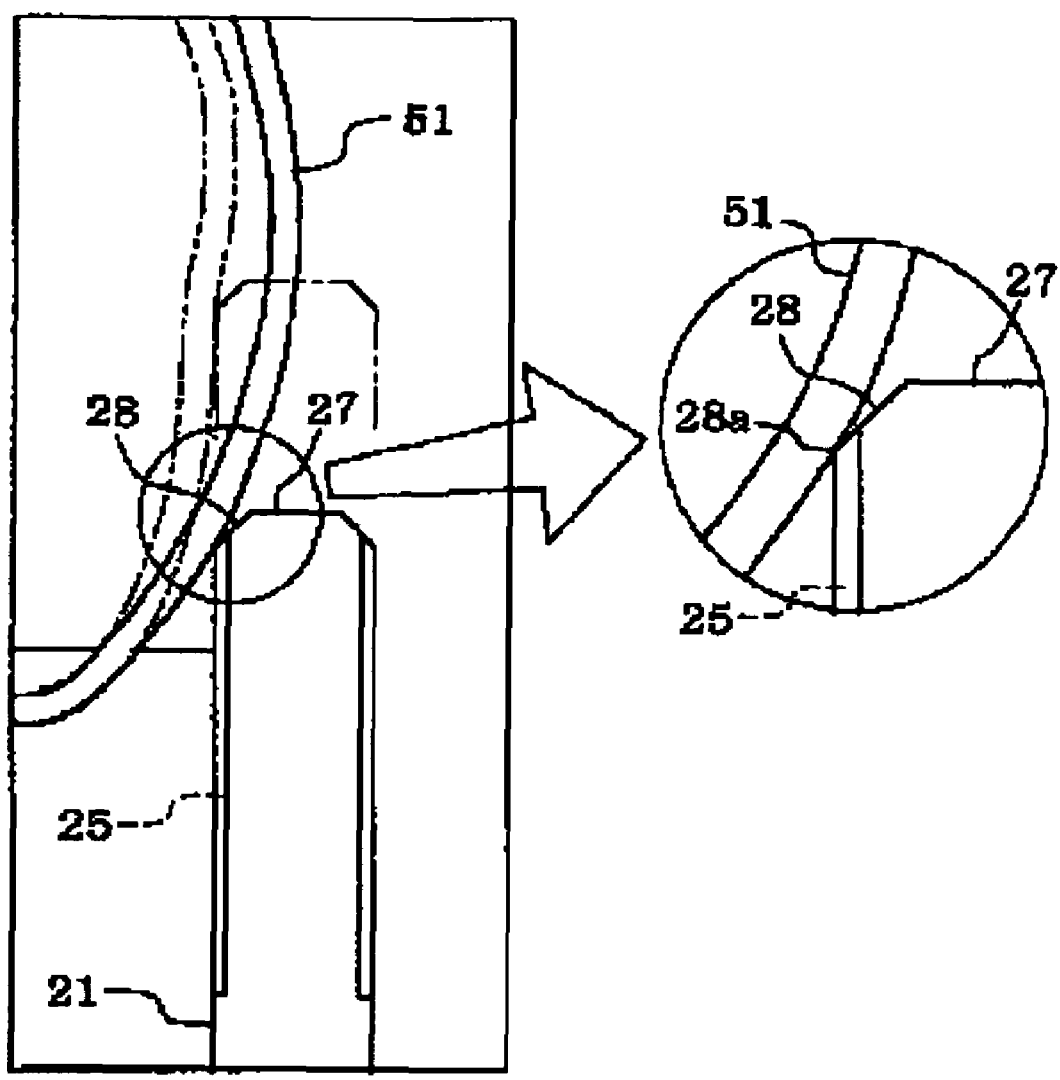
FIG. 13 is a view illustrating insertion of a conventional element having chamfers formed on a rear end.

In the above-described embodiment, a portion of each of the metallic terminal members 51 which comes into contact with the electrode terminal 25 is formed into the projection 57b. However, the projection 57b may also be omitted. In other words, the shape or structure of the metallic terminal member may be modified as appropriate. In each of the above-described metallic terminal members, a portion extending frontward from an end portion connected to a lead wire is turned back inwardly (toward an element side) to thereby provide a free end on the side toward the element, and a portion which comes into contact with the electrode terminal is provided on the same inward side as the free end. However, each of the metallic terminal members 51 may be formed as shown in FIG. 11; i.e., a front end portion of the curved portion 57 is turned back outwardly, so that the free end is provided on a side opposite the element 21. FIG. 11 corresponds to an enlarged view shown in FIG. 9. Since the shape of the metallic terminal member 51 is modified, the design of the metallic-terminal-member retainer 71 is modified accordingly. However, basically, no change is involved, so that like portions are denoted by like reference numerals, and no further description thereof is provided. In any event, the metallic terminal members are not limited thereto, and the present invention can be embodied while employing metallic terminal members having an appropriate shape. That is, the present invention can be widely applied to sensors having a terminal connection structure in which, by means of inserting, through relative movement, a sensor element from its rear end along its longitudinal direction, metallic terminal members are elastically deformed and pressed against corresponding electrode terminals formed on side surfaces of the sensor element to thereby be connected to the electrode terminals.

Also, no particular limitation is imposed on the structure and shape of the metallic-terminal-member retainer which is formed of an electrically insulative material and retains therein the metallic terminal members so as to establish electrical insulation between the metallic terminal members. The structure and shape of the metallic-terminal-member retainer can be modified as appropriate. The sensor of the present invention can be modified as appropriate in terms of structure and configuration without departing from the spirit or scope of the invention.

The present invention is embodied as a full range air/fuel ratio sensor. However, the present invention can be embodied as other types of sensors (such as an oxygen sensor, a $NO_x$ sensor, and a temperature sensor) so long as a terminal connection structure similar to that of the present invention is employed.

This application is based on Japanese Patent Application No. 2005-82639 filed Mar. 22, 2005, incorporated herein by reference in its entirety.

What is claimed is:

1. A sensor comprising:
   a sensor element including a detection portion formed at a front end portion adapted to face a measurement object, a rear end portion, a plurality of electrode terminals formed on a side surface of the rear end portion, and a chamfer provided on an edge defined by a rear end surface and the side surface having the electrode terminals formed thereon;
   a plurality of metallic terminal members elastically deformed and pressed against corresponding electrode terminals formed on the side surface of the sensor element so as to engage said sensor element; and
   an insulating retainer retaining therein said metallic terminal members and surrounding the rear end portion of the sensor element,
   wherein rear ends of the electrode terminals are spaced apart from a front end of the chamfer, and a flat surface of the sensor element is present between the rear ends of the electrode terminals and the front end of the chamfer, and
   wherein the distance between the rear ends of the electrode terminals and the front end of the chamfer as measured on the flat surface along the longitudinal direction of the sensor element is longer than the distance along the longitudinal direction between the front end of the chamfer and the rear end surface of the sensor element.

2. The sensor as claimed in claim 1, wherein the distance between the rear ends of the electrode terminals and the front end of the chamfer as measured on the flat surface along a longitudinal direction of the sensor element is 0.5 mm or more.

3. The sensor as claimed in claim 1, wherein the metallic terminal members include projections projecting toward corresponding electrode terminals, the projections pressing against the electrode terminals.

4. The sensor as claimed in claim 1, wherein each of the metallic terminal members includes a support portion extending along the longitudinal direction, and a turnback portion extending rearward along the longitudinal direction from a front end of the support portion; the turnback portion including a front end connected to the front end of the support portion and an abutment portion located rearward of the front end and adapted to abut the support portion; and the metallic terminal members are configured such that, in a free state before engaging the sensor element, the abutment portions are separated from the corresponding support portions and such that, as the metallic terminal members engage the front end of the sensor element so as to move the front ends of the turnback portions frontward beyond the front end of the chamfer located on the side toward the front end of the sensor element, the turnback portions are elastically deformed toward corresponding support portions, and the abutment portions come to abut the corresponding support portions.

5. A sensor comprising:
   a sensor element including a detection portion formed at a front end portion adapted to face a measurement object, a rear end portion, a plurality of electrode terminals formed on a side surface of the rear end portion, and a chamfer provided on an edge defined by a rear end surface and the side surface having the electrode terminals formed thereon;
   a plurality of metallic terminal members elastically deformed and pressed against corresponding electrode terminals formed on the side surface of the sensor element so as to engage said sensor element; and
   an insulating retainer retaining therein said metallic terminal members and surrounding the rear end portion of the sensor element,
   wherein rear ends of the electrode terminals are spaced apart from a front end of the chamfer, and a flat surface of the sensor element is present between the rear ends of the electrode terminals and the front end of the chamfer, and
   wherein each of the metallic terminal members includes a support portion extending along the longitudinal direction, and a turnback portion extending rearward along the longitudinal direction from a front end of the support portion; the turnback portion including a front end connected to the front end of the support portion and an abutment portion located rearward of the front end and adapted to abut the support portion; and the metallic terminal members are configured such that, in a free state before engaging the sensor element, the abutment portions are separated from the corresponding support portions and such that, as the metallic terminal members engage the front end of the sensor element so as to move the front ends of the turnback portions frontward beyond the front end of the chamfer located on the side toward the front end of the sensor element, the turnback portions are elastically deformed toward corresponding support portions, and the abutment portions come to abut the corresponding support portions.

* * * * *